(12) United States Patent
Sun et al.

(10) Patent No.: US 8,362,240 B2
(45) Date of Patent: Jan. 29, 2013

(54) TAXOL DERIVATIVES WITH ANTITUMOR ACTIVITY

(75) Inventors: Piaoyang Sun, Shanghai (CN); Xinsheng Lei, Shanghai (CN); Kaihong Yuan, Shanghai (CN)

(73) Assignee: Shanghai Hengrui Pharmaceutical Co., Ltd., Shangahi (CN)

( * ) Notice: Subject to any disclaimer, the term of this patent is extended or adjusted under 35 U.S.C. 154(b) by 461 days.

(21) Appl. No.: 12/160,456

(22) PCT Filed: Jan. 5, 2007

(86) PCT No.: PCT/CN2007/000022
§ 371 (c)(1),
(2), (4) Date: Jul. 10, 2008

(87) PCT Pub. No.: WO2007/079666

PCT Pub. Date: Jul. 19, 2007

(65) Prior Publication Data
US 2010/0168420 A1    Jul. 1, 2010

(30) Foreign Application Priority Data
Jan. 10, 2006 (CN) .......................... 2006 1 0001205

(51) Int. Cl.
C07D 413/14    (2006.01)
(52) U.S. Cl. .................................................... 544/148
(58) Field of Classification Search .................. 544/148
See application file for complete search history.

(56) References Cited

U.S. PATENT DOCUMENTS
6,646,123 B2 * 11/2003 Terasawa et al. ............... 544/60
6,677,456 B2    1/2004 Soga et al. ................. 546/284.1

FOREIGN PATENT DOCUMENTS
WO    WO 94/20088    9/1994

* cited by examiner

Primary Examiner — Rebecca Anderson
(74) Attorney, Agent, or Firm — Jon L. Woodard; MacDonald, Illig, Jones & Britton LLP

(57) ABSTRACT

Taxol derivatives or their salts having the formula as following: Wherein, $R_1$, $R_2$, $Z_1$, $Z_2$, $Z_3$ and $Z_4$ are defined as the description. Their preparation methods and their use as antitumor agent are also disclosed.

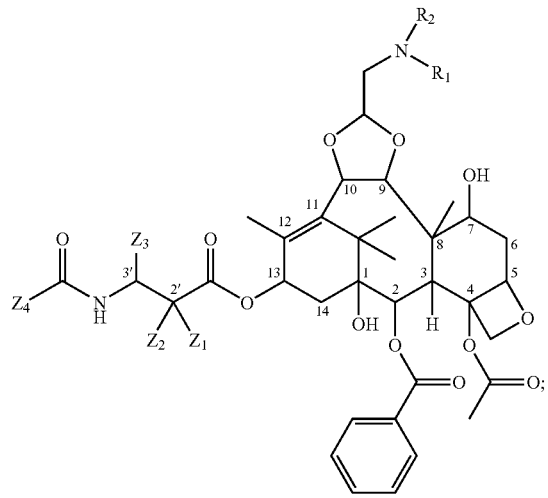

8 Claims, 1 Drawing Sheet

TAXOL DERIVATIVES WITH ANTITUMOR ACTIVITY

FIELD OF THE INVENTION

The present invention relates to a novel taxol derivatives with antitumor activity.

BACKGROUND OF THE INVENTION

Taxol is a natural compound having the following chemical formula, which can be obtained from a trunk of *Taxus brevifolia* in small quantities.

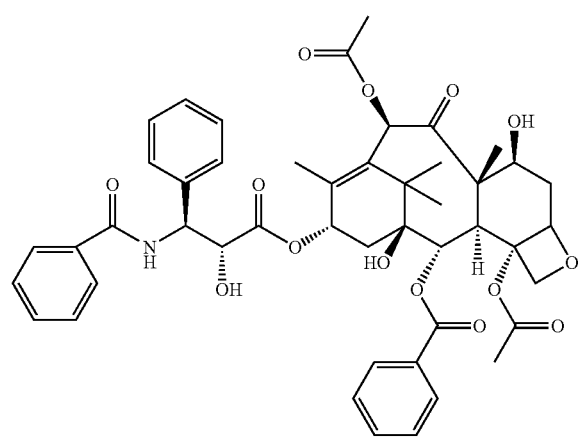 [SMILES: CC(=O)O[C@H]1C(=O)[C@]2(C)[C@@H](O)CC3OC[C@@]3(OC(C)=O)[C@H]2[C@H](OC(=O)c2ccccc2)[C@]2(O)C[C@H](OC(=O)[C@H](O)[C@@H](NC(=O)c3ccccc3)c3ccccc3)C(C)=C1C2(C)C]

It is known in the art that taxol has an antitumor activity and its action mechanism is based on the depolymerization inhibition action of microtubule during cell division, and thereby it was expected as an antitumor agent, which is different from the general antitumor agents in clinical application.

Although taxol can be only obtained naturally in extremely small quantities, recently the synthesis of taxol derivatives were disclosed by using a starting material 10-O-deacethyl-baccatinIII having the following structure:

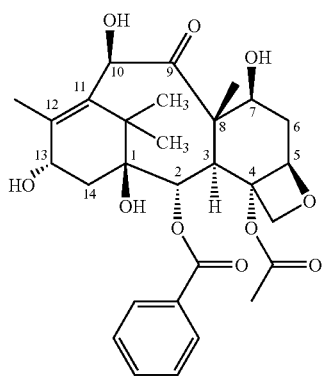

Compounds having the formula III as taxol precursors can be obtained from leaves and the like of taxaceous plants in relatively large quantities. Among the compounds, a compound (Taxotere™) having the following structure has drawn attention as a compound with an antitumor activity similar to or better than that of taxol and is now under development as an antitumor agent:

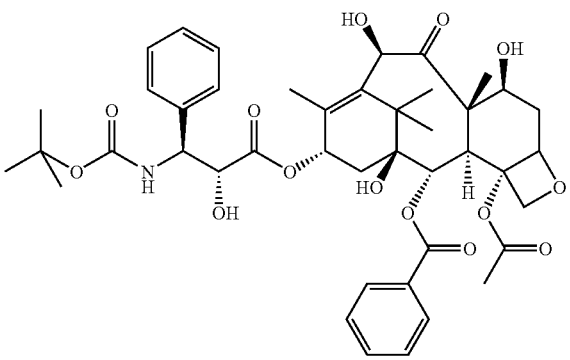 [SMILES: CC(=O)O[C@@]12COC1C[C@H](O)[C@@]1(C)C(=O)[C@H](O)C3=C(C)[C@@H](OC(=O)[C@H](O)[C@@H](NC(=O)OC(C)(C)C)c4ccccc4)C[C@@](O)([C@@H](OC(=O)c4ccccc4)[C@@H]12)C3(C)C]

Taxol and Taxotere™ are also the desired antitumor compounds. However, according to the clinical tests, it is known that these compounds have low efficacy on digestive organ cancers, especially large bowel cancers, so that great concern has been directed toward the development of derivatives that have stronger antitumor effect.

The 9-position of taxol derivatives is generally a ketone group, but some derivatives are also known in which 9-position is reduced. A compound having a α-configuration hydroxyl group at 9-position was obtained from a natural source, and various types of the 9-position α-hydroxyl group derivatives obtained by chemical modification of the compound have been reported. Also, it is known in the art that a compound having a β-configuration hydroxyl group at the 9-position can be synthesized chemically by reducing 10-O-deacethylbaccatin III using a reducing agent, and various types of the 9-position β-hydroxyl group derivatives obtained by chemical modification of the compound have been reported (for example, see in WO 94/20088).

As a result of extensive investigation, the present inventors have found that the antitumor activity of the aforementioned 9-position β-hydroxyl group taxol derivatives sharply increases when the 9-position hydroxyl group and 10-position hydroxyl group thereof are converted into cyclic acetal. The present invention has therefore been accomplished according to the above.

SUMMARY OF TIRE INVENTION

Accordingly, the present invention is directed to compounds having the following general formula or the salts thereof:

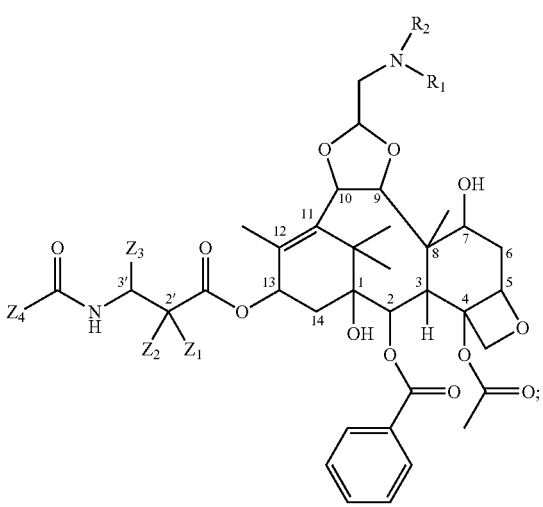

wherein:
R₁ or R₂ each independently represents hydrogen, alkyl, halogen-substituted alkyl, or the groups composed of R₁, R₂, N and/or O selected from the groups consisting of:

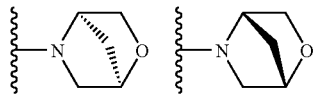

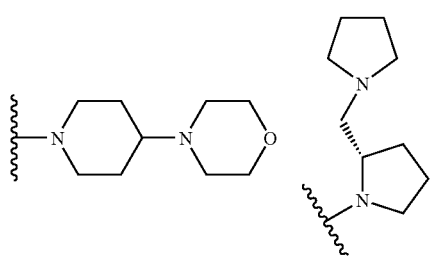

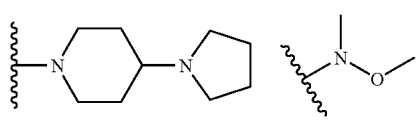

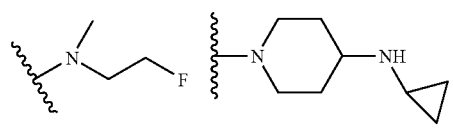

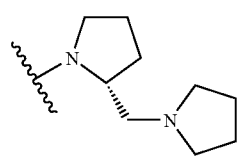

$Z_1$ represents hydrogen, hydroxyl, halogen, or alkyl;

$Z_2$ represents hydrogen, hydroxyl, halogen, or alkyl;

$Z_3$ represents alkyl, alkenyl, alkynyl, cycloalkyl, aryl or heterocyclic, wherein each of said alkyl, alkenyl, alkynyl, cycloalkyl, aryl or heterocyclic is optionally substituted by one or more groups selected from the group consisting of halogen, hydroxyl, carboxylic, alkyl, alkoxyl, aryl, amino, alkylamino, aminoalkyl, alkylaminoalkyl, alkoxyl carbonyl, aryloxy carbonyl, acyl, amido and acyloxy;

$Z_4$ represents alkyl, aryl or alkoxy, wherein each of said alkyl, aryl or alkoxy is optionally substituted by one or more groups selected from the group consisting of halogen, hydroxyl, carboxylic acid, alkyl, alkoxyl, phenyl, amino, alkylamino, aminoalkyl, alkylaminoalkyl, alkoxyl carbonyl, aryloxy carbonyl, acyl, amido and acyloxy;

Configuration of the 3'-position, to which the substituent group $Z^3$ is linked, can be one of both the configurations, but preferably the same configuration with natural taxol. Also, configuration of the 7-position is either α- or β-configuration.

Taxol derivatives of the present invention may be in the free form as such and in the form of an acid addition salt or a salt of carboxylic acid. Examples of acid addition salt include inorganic acid salts which comprise, but are not limited to sulfate, nitrate, hydrobromate, hydroiodate, and phosphate and organic acid salts which comprise, but are not limited to acetate, methane sulfonate, benzene sulfonate, toluene sulfonate, citrate, maleate, fumarate, and lactate.

Examples of salts of carboxyl group may be either inorganic salts or organic salts, which include alkali metal salts, such as lithium salt, sodium salt, potassium salt, alkaline earth metal salts, such as magnesium salt, calcium salt and the like, as well as ammonium salt, triethylamine salt, N-methylglucamine salt, tris-(hydroxymethyl)aminomethane salt and the like.

The preparation method of the compounds of the present invention is described as follows. During the reaction, the substituent groups may be protected with the protecting groups if desired, and the conversion sequence of each substituent group is not particularly limited.

Synthesis Methods:

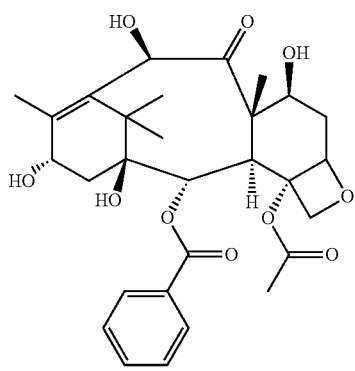 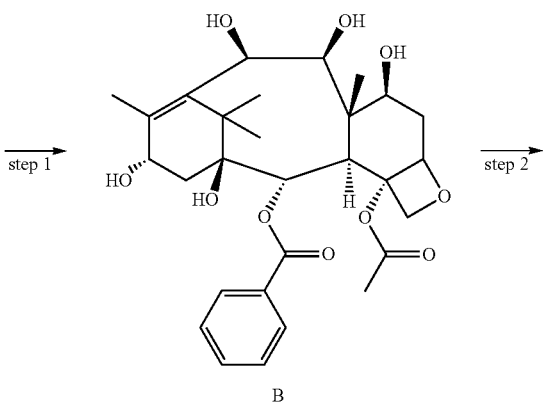

A  step 1  B  step 2

-continued
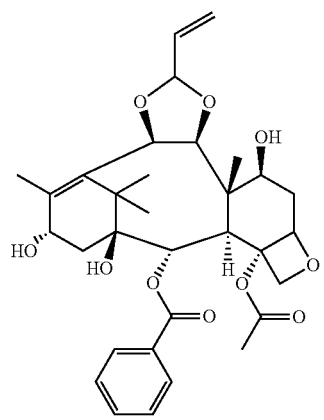
C
step 3
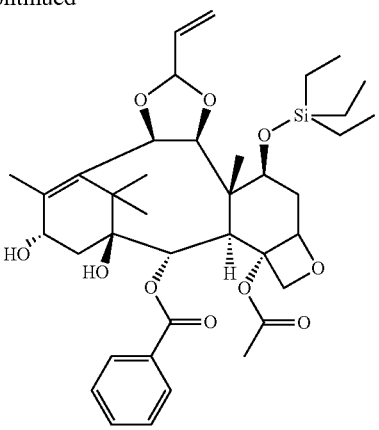
D
step 4
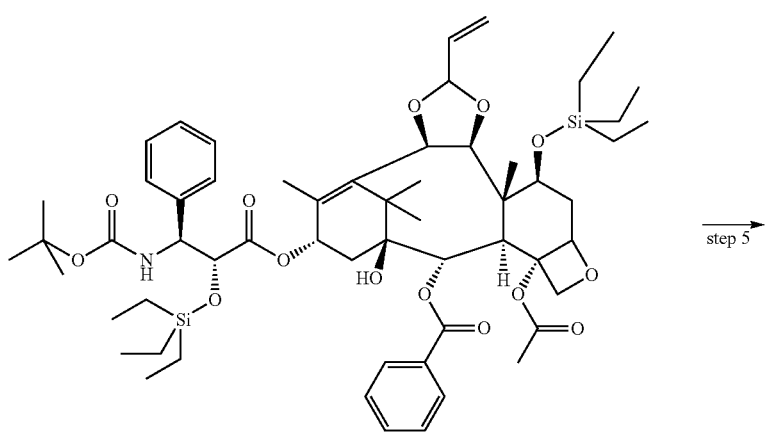
E
step 5
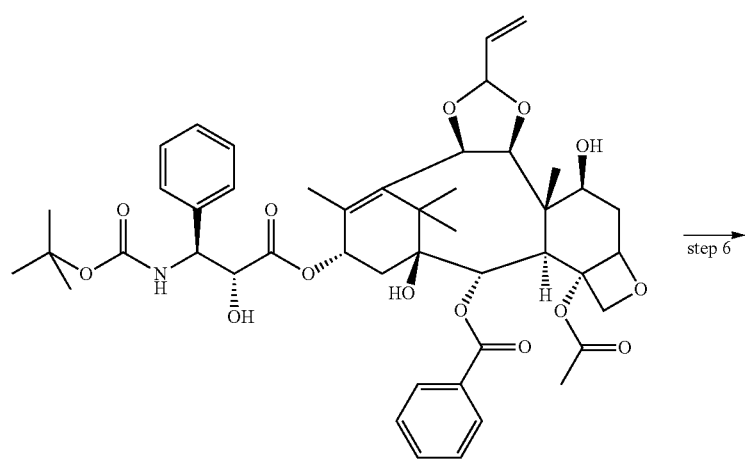
F
step 6

-continued
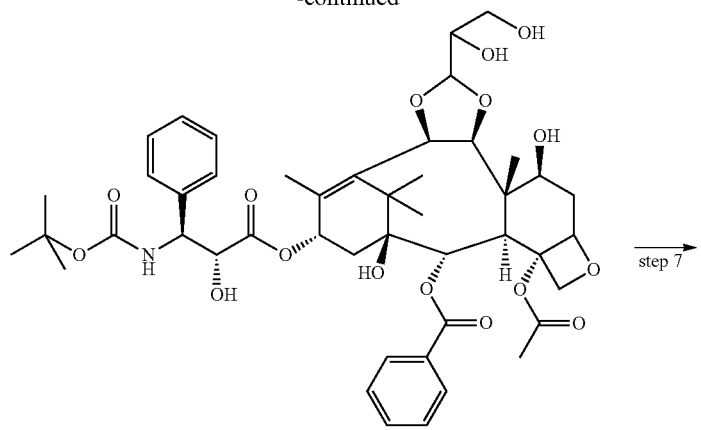
G
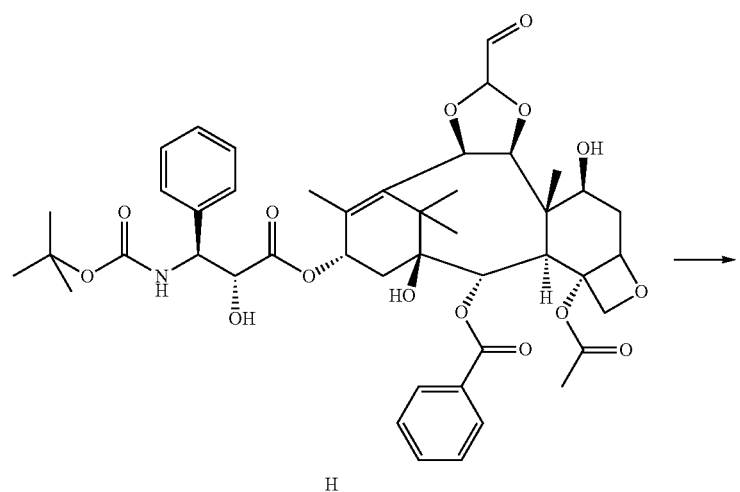
H
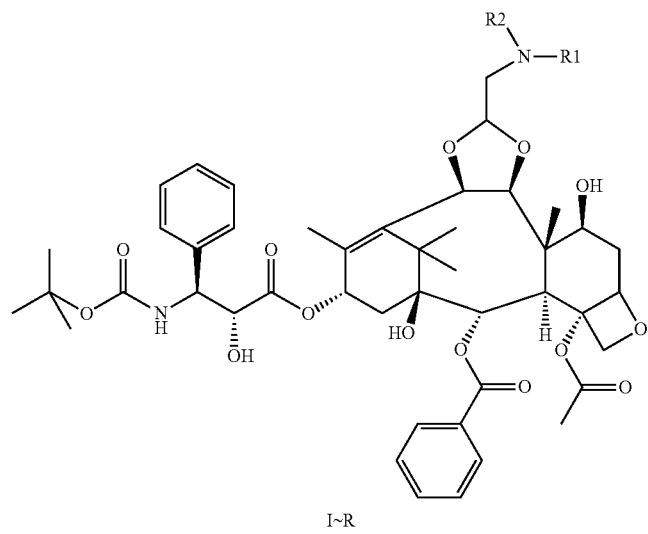
I~R

In the above reaction scheme, $R_1$ or $R_2$ each independently represents hydrogen, alkyl, halogen-substituted alkyl, or the groups composed of $R_1$, $R_2$, N and/or O selected from the groups consisting of:

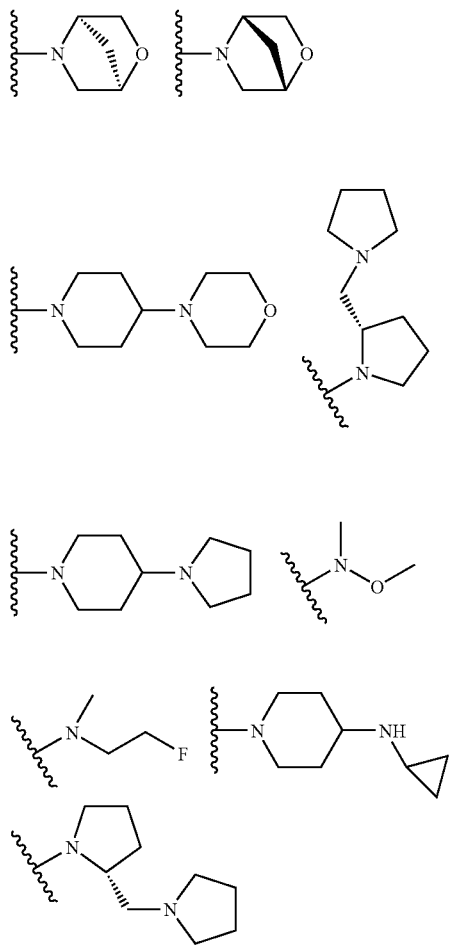

The compounds of the present invention can be used in the treatment of various cancers, such as lung cancers, digestive organ cancers, ovary cancers, uterine cancers, breast cancers, liver cancers, head and neck cancers, blood cancers, renal cancers, testicular tumors and the like.

Suitable administration routes of the compounds of the present invention may include, but are not limited to various injections, such as intravenous, intramuscular, subcutaneous and the like or other various routes of administration such as oral administration, transdermal absorption and the like. The preferred routes of administration are intravenous injection by the solutions and oral. The solutions can be prepared by forming an acid addition with a pharmacologically acceptable acid or the metal salt of alkali, such as sodium and the like. In the case of oral administration, the compounds may be in its free form or salt form.

Suitable pharmaceutical formulations can be selected according to the various administrations of the present invention and formulated in conventional manner. In the dosage forms of the antitumor agent of the present invention, examples of oral administrations include tablets, powders, granules, capsules, solutions, syrups, elixirs, oil or aqueous suspensions and the like. In the case of injection administrations, stabilizing agents, antiseptics, solubilizing agents and the like may be used in the formulations. The auxiliary agents containing injections may be dispensed into containers and made of the solid formulations by freeze-drying and the like, which can be dissolved again before use.

Liquid formulations include solutions, suspensions, emulsions and the like. Suspending agents, emulsifying agents and the like may be used as the additives when the formulations are prepared.

The compounds of the present invention can be used for the treatment of cancers in mammals, particularly in human. In the case of human, it may preferably be administered once a day repeatedly at appropriate intervals.

The dosage of administration is about 0.5 to about 50 $mg/m^2$ of body surface, preferably about 1 to about 20 $mg/m^2$ of body surface.

DETAILED DESCRIPTION OF THE INVENTION

Figure 1:
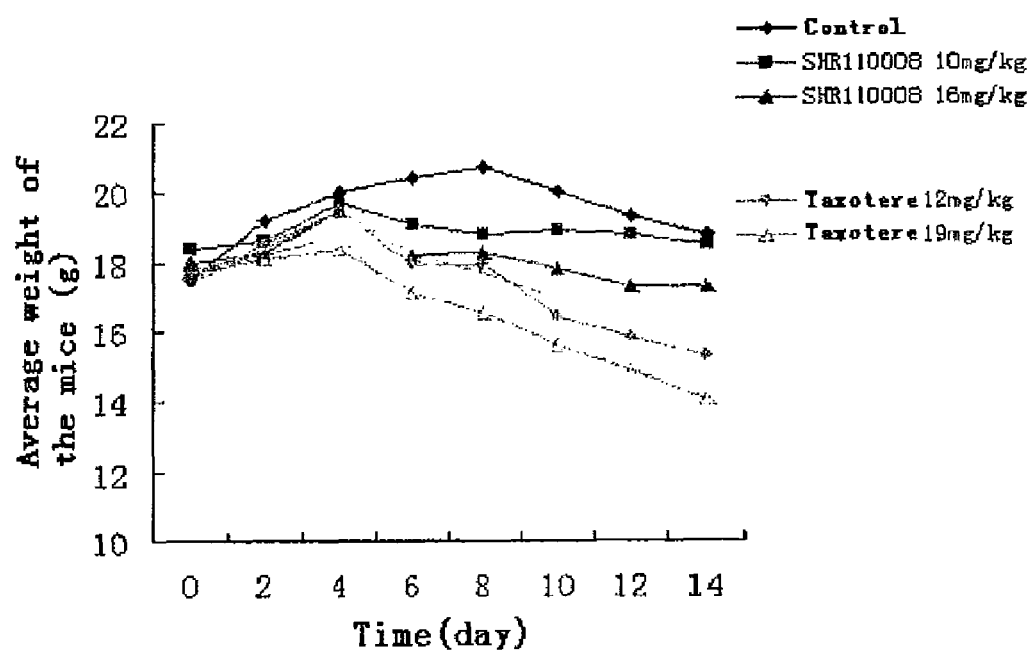
FIG. 1 is the weight effect of compounds SHR-110008 and Taxotere against tumors in nude mice.

The following examples and the test examples are provided to the skilled person in the art to more clearly understand and practice the present invention, which should not be considered as limiting the scope of the invention, but merely as being illustrative and representative thereof.

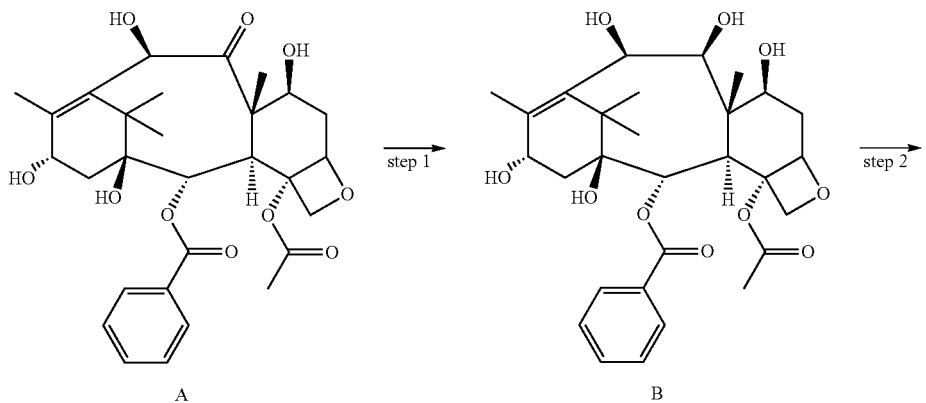

-continued
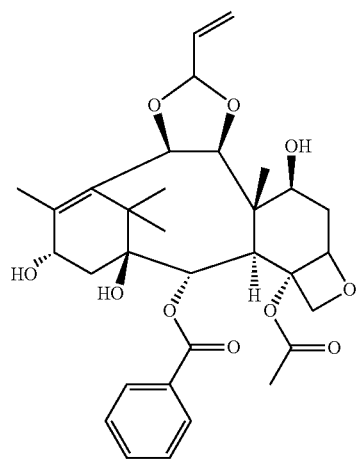
C
step 3
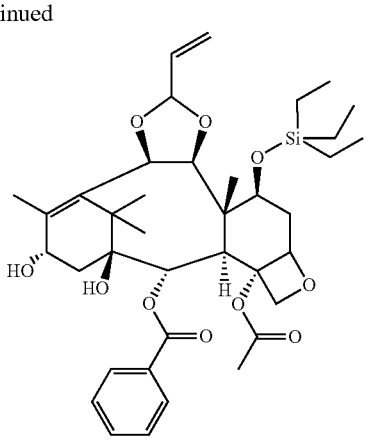
D
step 4
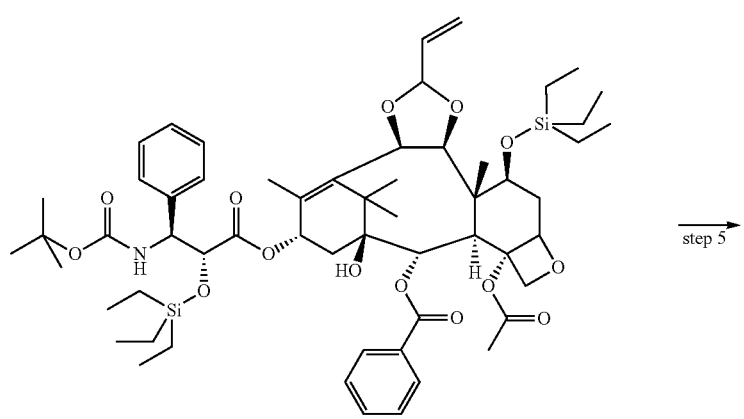
E
step 5
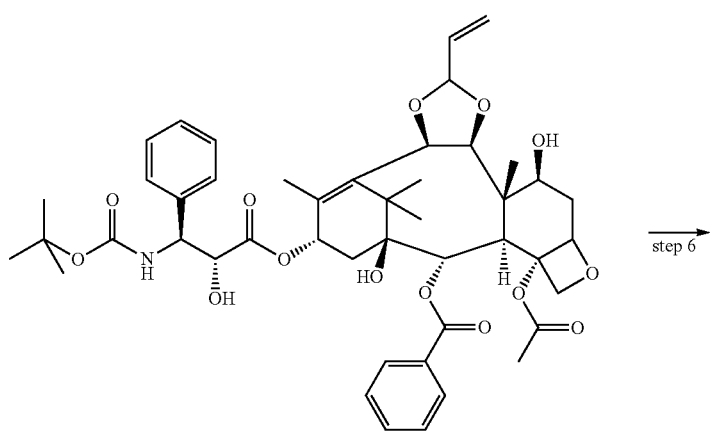
F
step 6

-continued
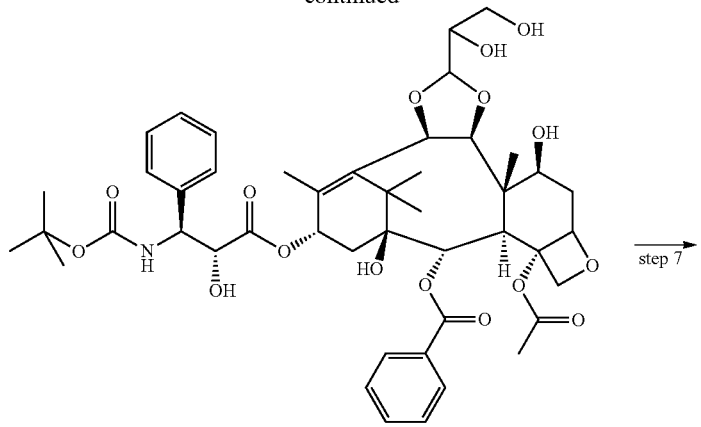
G
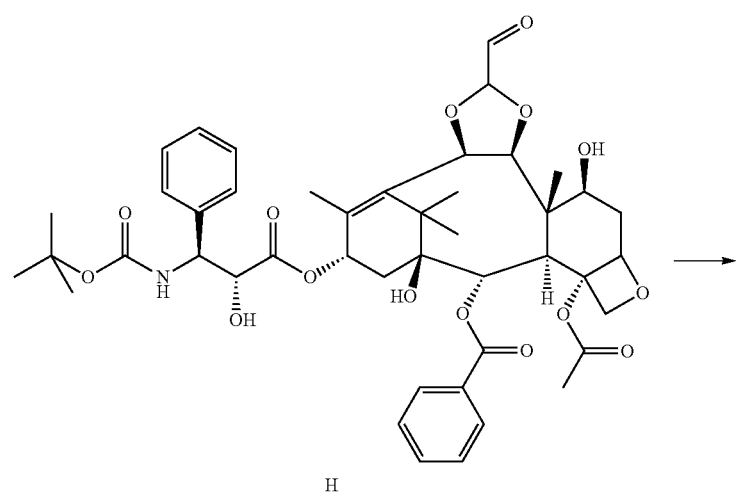
H
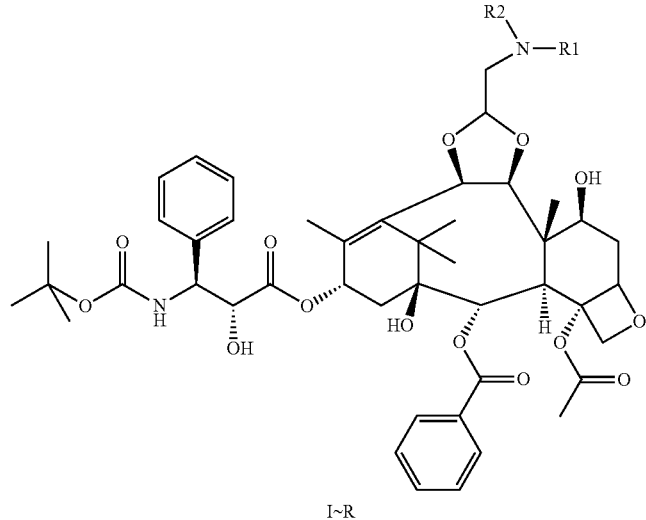
I~R

Step 1

9β-10-deacetyl-9-dihydro baccatinIII

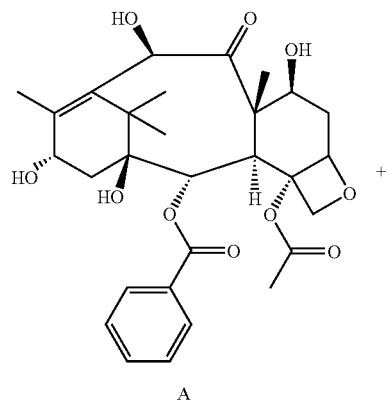

A

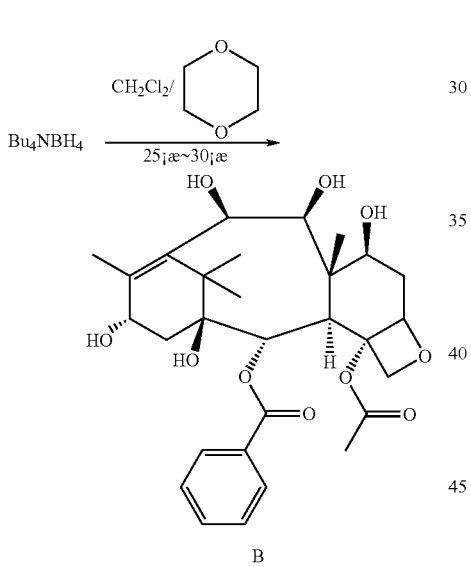

B 10-deacetylbaccatin III A (1.4 g, 2.57 mmol, 1.0 eq), 40 ml anhydrous dichloromethane and 40 ml anhydrous 1,4-dioxane was added into a 250 ml dry three-neck flask to obtain a solution while maintaining the temperature at 25° C.~30° C. under an argon atmosphere. Tert-butylammonium borohydride (2.65 g, 0.3 mmol, 4.0 eq) was then added into the solution under stirring to form a mixture. Upon completion of the addition, the mixture was stirred at 25° C.~30° C. for 19 hours. It is shown that the starting materials were completely reacted during the reaction according to the Point-plate tracking (ethyl acetate:methanol=40:1). The mixture was cooled down in an ice/salt bath and adjusted to pH 6 with 1N hydrochloric acid solution. And then, water was added into the mixture quickly and the ice bath was removed. The mixture was stirred for 0.5-1 hour. The mixture was extracted with ethyl acetate (100 mL×4) to obtain the organic extracts. The combined organic extracts were washed with water (25 ml×1) and saturated brine (25 ml×1), dried with anhydrous sodium sulfate over night, filtered and concentrated under reduced pressure to obtain a residue. The residue was purified by silica gel column chromatography with hexane:ethyl acetate:methanol=15:25:1) as eluents to provide 9β-10-deacetyl-9-dihydro baccatinIII B (1.2 g, a white-like solid) with the yield of 85%.

Rf=0.42 (ethyl acetate:methanol=40:1(V/V)).

MW=546, ESI-MS: [M+H]$^+$=547.

$^1$H-NMR (CD$_3$OD, 400 MHz): δ8.11-7.4 (m, 5H, Ar—H), 6.1 (d, J=5.3 Hz, 1H, C$_2$—H), 5.1 (d, J=5.7 Hz, 1H, C$_{10}$—H), 5.0 (d, J=8.9 Hz, 1H, C$_5$—H), 4.8 (b, 1H, C$_{13}$—H), 4.6-4.5 (d, J=5.7 Hz, 1H, C$_9$—H), 4.3-4.2 (d, J=7.7 Hz, 1H, C$_{20}$—H$_\alpha$), 4.2-4.1 (d, J=7.7 Hz, 1H, C$_{20}$—H$_\beta$), 3.9 (dd, 0.1-7.3 Hz, J'=9.7 Hz, 1H, C$_7$—H), 3.3-3.2 (d, J=4.9 Hz, 1H, C$_3$—H), 2.6-2.4 (m, 1H, C$_6$—H$_\alpha$), 2.4-2.3 (m, 1H, C$_{14}$—H$_\alpha$), 2.3-2.2 (m, 1H, C$_{14}$—H$_\beta$), 2.2 (s, 3H, Ac—CH$_3$), 1.9 (s, 3H, C$_{18}$—H), 1.9-1.8 (m, 1H, C$_6$—H$_\beta$), 1.7 (s, 3H, C$_{16}$—H), 1.6 (s, 3H, C$_{19}$—H), 1.2 (s, 3H, C$_{17}$—H).

Step 2

9β-10-deacetyl-9-dihydro-9,10-O-(2-allylidene)baccatinIII

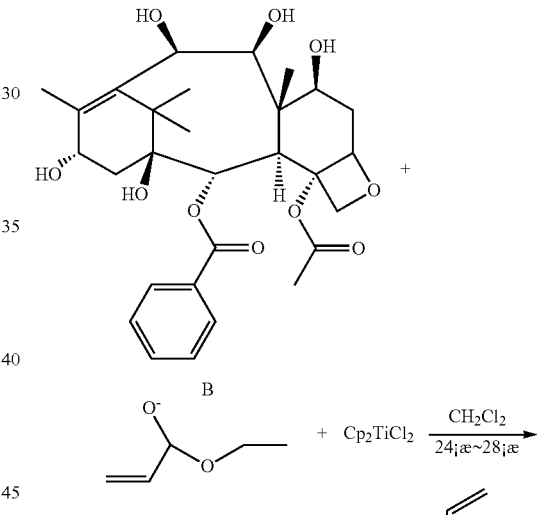

C

The resulting compounds from step 1, 9β-10-deacetyl-9-dihydro baccatinIII B (1.2 g, 2.20 mmol, 1.0 eq) was suspended in 60 ml anhydrous dichloromethane to form a solution. Acrolein diethyl acetal (1.68 ml, 11.0 mmol, 5.0 eq) and bis(cyclopentadienyl) titanium (IV) dichloride (0.05 g, 0.22 mmol, 0.2 eq) were then added into the solution with stirring under an argon atmosphere to form a mixture. Upon completion of the addition, the mixture was stirred for 18 hours while maintaining the temperature at 24° C.~28° C. It is shown that the starting materials were completely reacted during the reaction according to the Point-plate tracking (ethyl acetate: methanol=40:1). The reaction was quenched with triethylamine (adjusted to pH 7), and the solution removed by spinning steaming under reduced pressure to obtain a residue. The residue was purified by silica gel column chromatography with hexane:ethyl acetate=1:1 as eluents to provide 9β-10-deacetyl-9-dihydro-9,10-O-(2-allylidene)baccatinIII C (0.979 g, a white-like solid) with the yield of 75.9%.

Rf=0.44 (eluents: hexane:ethyl acetate=1:1(V/V)).
MW=584, ESI-MS: [M+H]$^+$=585.
$^1$H-NMR (CD$_3$Cl$_3$, 400 MHz): δ8.2-7.4 (m, 5H, Ar—H), 6.2-5.9 (m, 1H, CH$_2$=CH—), 6.1-6.0 (d, J=5.7 Hz, 1H, C$_2$—H), 5.6-5.5 (d, J=17.4 Hz, 1H, trans-CH$_2$=CH—), 5.5-5.4 (d, J=10.9 Hz, 1H, cis-CH$_2$=CH—), 5.3 (d, J=7.3 Hz, 1H, C$_{10}$—H), 5.2 (d, J=6.1 Hz, 1H, C$_5$—H), 5.1 (s, 1H, OH), 4.8 (b, 1H, C$_{13}$—H), 4.6 (d, J=8.1 Hz, 1H, CH$_2$=CH—), 4.4 (d, J=8.5 Hz, 1H, C$_{20}$—H$_\alpha$), 4.3 (d, J=8.5 Hz, 1H, C$_{20}$—H$_\beta$), 4.1 (m, 1H, C$_7$—H), 3.9 (d, J=6.9 Hz, 1H, C$_9$—H), 3.1-3.0 (d, J=5.3 Hz C$_3$—H), 2.4-2.3 (m, 1H, C$_6$—H$_\alpha$), 2.4-2.3 (s, 3H, Ac—CH$_3$), 2.3-2.1 (m, 2H, C$_{14}$—H), 2.0-1.9 (m, 1H, C$_6$—H$_\beta$), 1.9 (s, 3H, C$_{18}$—H), 1.8 (s, OH), 1.7-1.6 (s, 3H, C$_{16}$—H), 1.6 (s, 3H, C$_{19}$—H), 1.3-1.2 (s, OH), 1.2 (s, 3H, C$_{17}$—H).

Step 3

9β-10-deacetyl-9-dihydro-9,10-O-(2-allylidene)-7-O-triethylsilyl baccatinIII

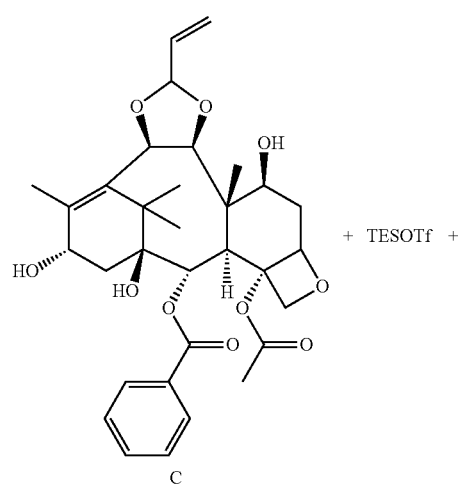

C

+ TESOTf +

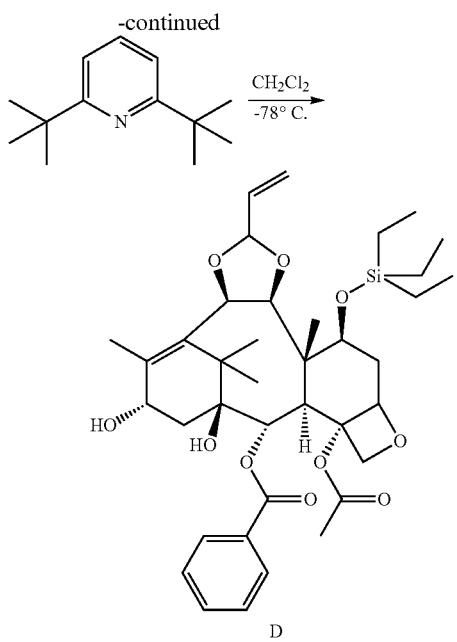

D

The resulting compound from step 2, 9β-10-deacetyl-9-dihydro-9,10-O-(2-allylidene) baccatinIII C (2.298 g, 3.93 mmol, 1.0 eq) was dissolved in anhydrous dichloromethane (378 ml) in a 500 ml dry three-neck flask under an argon atmosphere to obtain a solution. After cooling in dry ice/acetone bath, 2,6-di-tert-butyl-pyridine (1.27 g, 5.62 mmol, 1.56 eq) was added into the solution while maintaining the temperature at −78° C., then triethylsilyl trifluoromethanesulfonate (1.38 ml, 6.13 mmol, 1.56 eq) was added dropwise slowly to the solution to obtain a mixture. Upon completion of the addition, the mixture was stirred at −78° C. for 40 minutes. It is shown that the starting materials were completely reacted during the reaction according to the Point-plate tracking (hexane:ethyl acetate=2:1). The reaction was quenched by adding the saturated aqueous sodium bicarbonate (50 ml). The dry ice/acetone bath was removed, and the temperature was warmed to room temperature. The mixture was separated to organic phase and water phase. The water phase was extracted with ethyl acetate (100 ml×4) to obtain the organic extracts. The combined organic extracts were washed with saturated brine (25 ml×1), dried with anhydrous sodium sulfate, filtered and concentrated under reduced pressure to obtain a residue. The residue was purified by silica gel column chromatography with hexane:ethyl acetate=3:1 as eluents to provide 9β-10-deacetyl-9-dihydro-9,10-O-(2-allylidene)-7-O-triethylsilyl baccatinIII D (2.208 g, foam or wax solid) with the yield of 80.8%.

Rf=0.49 (eluents: hexane:ethyl acetate=1:1 (V/V)).
MW=698, ESI-MS: [M+H]$^+$=699.
$^1$H-NMR (CD$_3$Cl$_3$, 400 MHz): δ8.2-7.4 (m, 5H, Ar—H), 6.3-6.1 (m, 1H, CH$_2$=CH—), 5.9 (d, J=5.3 Hz, 1H, C$_2$—H), 5.6-5.5 (d, J=17.8 Hz, 1H, trans-CH$_2$=CH—), 5.5-5.4 (d, J=10.7 Hz, 1H, cis-CH$_2$=CH—), 5.4-5.3 (d, J=8.5 Hz, 1H, C$_{10}$—H), 5.1 (d, J=6.1 Hz, 1H, C$_5$—H), 4.9-4.7 (m, 1H, C$_9$—H), 4.8-4.7 (b, 1H, C$_{13}$—H), 4.6 (b, 1H, OH), 4.4-4.3 (d, AB-type, J=8.5 Hz, 2H, C$_{20}$—H), 4.0-3.9 (m, 1H, C$_7$—H), 3.2 (d, J=5.3 Hz, 1H, C$_3$—H), 2.3 (s, 3H, Ac—CH$_3$), 2.5-2.0

(m, 4H, C$_6$—H, C$_{14}$—H), 2.0-1.9 (s, 1H, C$_{18}$—H), 1.8-1.7 (s, 1H, OH), 1.6 (s, 3H, C$_{16}$—H), 1.6-1.5 (s, 3H, C$_{19}$—H), 1.1 (s, 3H, C$_{17}$—H), 1.1-0.9 (t, J=7.7 Hz, 9H, SiCH$_2$C̲H̲$_3$), 0.7-0.6 (q, J=7.7 Hz, 6H, SiC̲H̲$_2$CH$_3$).

Step 4

9β-13-O-[(2R,3S)-3-(tert-butyloxycarbonylamino)-2-(triethylmethylsiloxy)-3-phenyl propionyl]-10-deacetyl-9-dihydro-9,10-O-(2-allylidene)-7-O-triethylsilyl baccatinIII

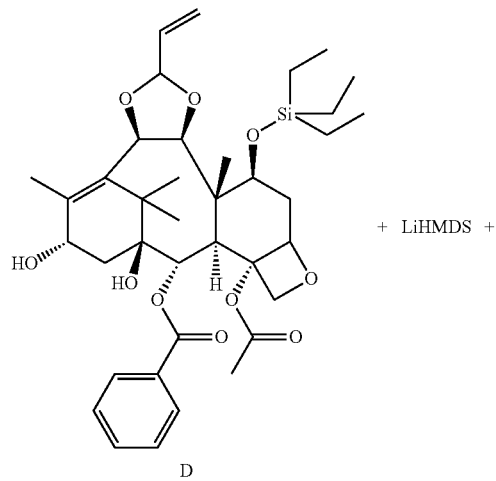

D

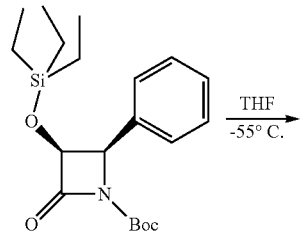

THF
-55° C.

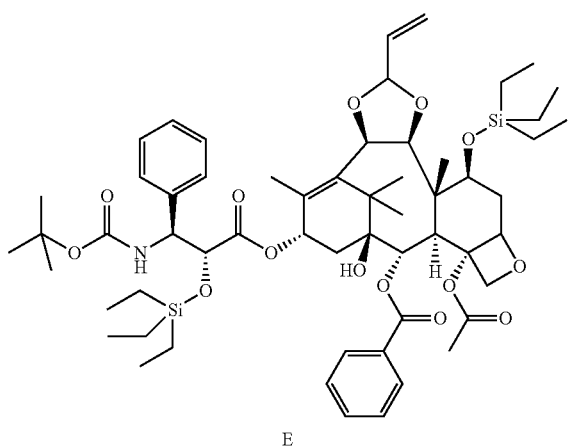

E

The resulting compounds from step 3, 9β-10-deacetyl-9-dihydro-9,10-O-(2-allylidene)-7-O-triethylsilyl baccatinIII D (1.85 g, 2.65 mmol, 1.0 eq) was dissolved in 68.5 ml anhydrous tetrahydrofuran under an argon atmosphere and cooled down to −55° C. to obtain a first solution. During slow stirring, a solution of lithium hexamethyldisilazide in anhydrous tetrahydrofuran (4 ml, 1M/L, 1.5 eq) was added dropwise to the first solution to obtain a second solution while stirring under the temperature of −55° C. in 0.5 hour. A solution of (3R,4R)-1-(tert-butylcarboxylic)-3-(triethylmethylsiloxy)-4-phenylnitroheterobutyl-2-one (3.02 g, 8.0 mmol, 3.0 eq) in anhydrous tetrahydrofuran (21.5 ml) was added dropwise to the second solution to form a mixture. Upon completion of the addition, the dry ice/acetone is removed. The mixture was stirred for 0.5~1 hour in the ice/water bath and added with 180 ml saturated aqueous sodium bicarbonate. Upon completion of the addition, the mixture was extracted with ethyl acetate (180 mL×4) to form the organic extracts. The combined organic extracts were washed with saturated brine (50 ml×1), dried with anhydrous sodium sulfate, filtered and concentrated under reduced pressure. The residue was purified by silica gel column chromatography with hexane:ethyl acetate=8:1 as eluents to provide 9β-13-O-[(2R,3S)-3-(tert-butyloxycarbonylamino)-2-(triethylmethylsiloxy)-3-phenylpropionyl]-10-deacetyl-9-dihydro-9,10-O-(2-allylidene)-7-O-triethylsilyl baccatinIII E (2.432 g, white-like solid) with the yield of 85.6%.

Rf=0.34 (hexane:ethyl acetate=8:1(V/V)).

MW=1075, ESI-MS: [M+H]$^+$=1076.

$^1$H-NMR (CD$_3$Cl$_3$, 400 MHz): δ8.2-7.2 (m, 10H, Ar—H), 6.3-6.0 (m, 2H), 5.9 (d, J=53 Hz, 1H, C$_2$—H), 5.6-5.5 (d, J=17.5 Hz, 1H, trans-C̲H̲$_2$=CH—), 5.5-5.4 (d, J=10.4 Hz, 1H, cis-CH$_2$=C̲H̲—), 5.6-5.4 (m, 1H, C$_9$—H), 5.3-5.2 (d, J=9.1 Hz, 1H, C$_{10}$—H), 5.1-5.0 (d, J=5.9 Hz, 1H, C$_5$—H), 4.9-4.8 (m, 1H), 4.6 (d, J=8.8 Hz, 1H), 4.6-4.5 (b, 1H, OH), 4.5-4.3 (d, AB-type, J=8.5 Hz, 2H, C$_{20}$—H), 4.0-3.9 (dd, 1H, J=5.1 Hz, J'=10.5 Hz), 3.2 (d, J=5.6 Hz, 1H), 2.5 (s, 3H, Ac—CH$_3$), 2.5-2.0 (m, 5H), 1.8 (s, 3H), 1.6-1.5 (s, 12H, t-Bu, CH$_3$), 1.4-1.3 (s, 3H), 1.3-1.2 (s, 3H), 1.1-0.9 (t, J=7.8 Hz, 9H), 0.8-0.7 (t, J=8.0 Hz, 9H), 0.7-0.6 (m, 6H), 0.5-0.3 (m, 6H).

Step 5

9β-13-O-[(2R,3S)-3-(tert-butyloxycarbonylamino)-2-hydroxyl-3-phenyl propionyl]-10-deacetyl-9-dihydro-9,10-O-(2-allylidene) baccatinIII

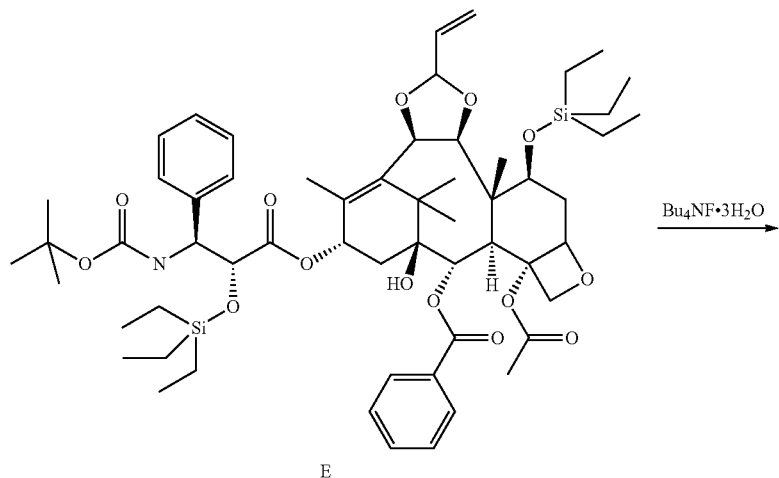

E

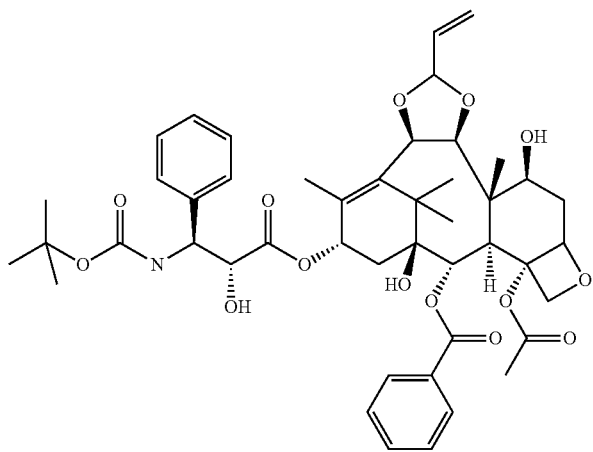

F

The resulting compound from step 4, 9β-13-O-[(2R,3S)-3-(tert-butyloxycarbonyl amino)-2-(triethylmethylsiloxy)-3-phenylpropionyl]-10-deacetyl-9-dihydro-9,10-O—-(2-allylidene)-7-O-triethylsilyl baccatinIII E (0.819 g, 0.761 mmol, 1.0 eq) was added into 10 ml anhydrous tetrahydrofuran in a 100 ml dry three-neck flask to form a solution under an argon atmosphere. A solution of tetrabutylammonium fluoride trihydrate (0.96 g, 3.04 mmol, 4.0 eq) in 10 ml anhydrous tetrahydrofuran was added dropwise into the solution in an ice/salt bath for 30 minutes. The reaction mixture was added with 40 ml saturated brine and 40 ml ethyl acetate, extracted with ethyl acetate (100 mL×4) to form the organic extracts. The combined organic extracts were dried with anhydrous sodium sulfate, filtered and concentrated under reduced pressure to form a residue. The residue was purified by silica gel column chromatography with hexane:ethyl acetate:methanol=25:15:1 as eluents to provide: 9β-13-O-[(2R,3S)-3-(tert-butyloxycarbonylamino)-2-hydroxyl-3-phenylpropionyl]-10-deacetyl-9-dihydro-9,10-O-(2-allylidene)baccatinIII F (0.596 g, white-like solid) with a yield of 92.4%.

Rf=0.38 (hexane:ethyl acetate:methanol=25:15:1(V/V)).

MW=847, ESI-MS: [M+H]$^+$=848.

$^1$H-NMR (CD$_3$Cl$_3$, 400 MHz): δ8.2-7.2 (m, 10H, Ar—H), 6.2-5.9 (m, 3H), 5.7-5.6 (d, J=9.9 Hz, 1H), 5.6-5.5 (d, J=16.9 Hz, 1H, trans-CH$_2$=CH—), 5.5-5.4 (d, J=10.5 Hz, 1H, cis-CH$_2$=CH—), 5.4-5.2 (m, 1H), 5.3 (d, J=7.2 Hz, 1H), 5.2 (d, J=6.4 Hz, 1H, CH$_2$=CH—), 5.1 (6, 1H, OH), 4.7-4.6 (b, 1H), 4.6-4.5 (d, J=7.8 Hz, 1H), 4.4-4.2 (dd, AB-type, J=8.6 Hz, 2H, C$_{20}$—H), 4.2 (b, 1H), 4.1 (m, 1H), 3.9-3.8 (d, J=7.0 Hz, 1H), 2.9 (d, J=4.8 Hz, 1H), 2.4-2.3 (dd, J=9.8 Hz, J'=15.2 Hz, 1H), 2.3 (s, 3H, Ac—CH$_3$), 2.3-2.0 (m, 3H), 1.9 (s, 1H), 1.7 (s, 3H, CH$_3$), 1.6 (s, 31-1, CH$_3$), 1.6-1.5 (s, 3H, CH$_3$), 1.4 (s, 9H, t-Bu), 1.3 (s, 3H, CH$_3$).

Step 6

9β-13-O-[(2R,3S)-3-(tert-butyloxycarbonylamino)-2-hydroxyl-3-phenyl propionyl]-10-deacetyl-9-dihydro-9,10-O-(2,3-dihydroxyl propylidene) baccatinIII

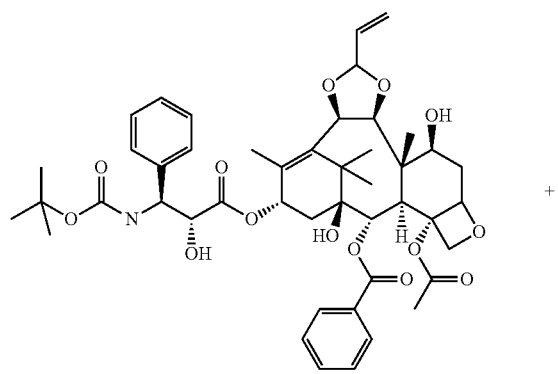

F

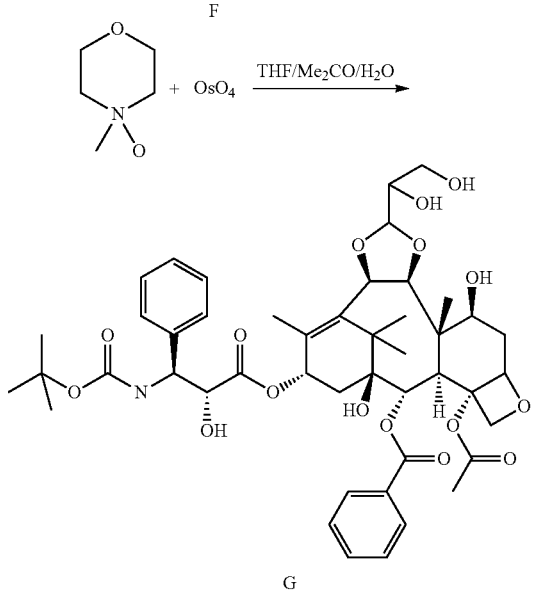

G

The resulting compound from step 5, 9β-13-O-[(2R,3S)-3-(tert-butyloxycarbonyl amino)-2-hydroxyl-3-phenylpropionyl]-10-deacetyl-9-dihydro-9,10-O-(2-allylidene)baccatinIII F (0.596 g, 0.703 mmol, 1.0 eq) was further added into N-methyl-morpholine N-oxide (0.412 g, 3.51 mmol, 5.0 eq) in a 100 ml three-neck flask under an argon atmosphere to obtain a first solution, and then the first solution was dissolved in a mixed solution of 15 ml tetrahydrofuran, 15 ml acetone and 15 ml water to form a second solution. Under stirring, a solution of osmium tetroxide (0.725 ml, 35.7 mg, 0.2 eq) in tert-butyl alcohol was added into the second solution to form a mixture, while maintaining the temperature under 28° C. over night. Upon completion of the addition, the mixture was quenched with 90 ml 10% aqueous solution of sodium thiosulfate, stirred in 10 minutes, and extracted with ethyl acetate (100 mL×3) to obtain the organic extracts. The combined organic extracts were washed with 25 ml saturated aqueous sodium bicarbonate and 25 ml saturated brine, dried with anhydrous sodium sulfate, filtered and concentrated under reduced pressure to form a residue. The residue was purified by silica gel column chromatography with dichloromethane: methanol=20:1 as eluents to provide 9β-13-O-[(2R,3S)-3-(tert-butyloxycarbonylamino)-2-hydroxyl-3-phenylpropionyl]-10-deacetyl-9-dihydro-9,10-O-(2,3-dihydroxyl propylidene) baccatinIII G (0.61 g, white-like solid) with a yield of 98%.

Rf-0.24 (dichloromethane:methanol=20:1(V/V)).
MW=881, ESI-MS: [M+H]$^+$=882.
$^1$H-NMR (CD$_3$Cl$_3$, 400 MHz): δ8.2-7.2 (m, 10H, Ar—H), 6.2-6.1 (m, H), 6.1-6.0 (d, J=5.4 Hz, 1H), 5.7-5.6 (m, 1H), 5.4-5.2 (m, 2H), 5.1 (s, 1H), 4.9 (d, J=6.5 Hz, 1H), 4.9-4.7 (m, 1H), 4.6 (s, 1H), 4.5-4.2 (dd, AB-type, J=8.5 Hz, 2H), 4.2-4.0 (m, 2H), 4.0-3.7 (m, 5H), 2.9 (d, J=6.8 Hz, 1H), 2.5-2.3 (dd, J=9.8 Hz, J'=15.2 Hz, 1H), 2.3 (s, 3H), 2.3-2.2 (m, 2H), 2.2-2.0 (m, 2H), 1.9 (b, 1H), 1.7 (s, 3H, CH$_3$), 1.65 (s, 3H, CH$_3$), 1.4 (s, 9H, t-Bu), 1.4-1.3 (s, 3H, CH$_3$, two isomers).

Step 7

9β-13-O-[(2R,3S)-3-(tert-butyloxycarbonylamino)-2-hydroxyl-3-phenyl propionyl]-10-deacetyl-9-dihydro-9,10-O-acetaldehydebaccatinIII

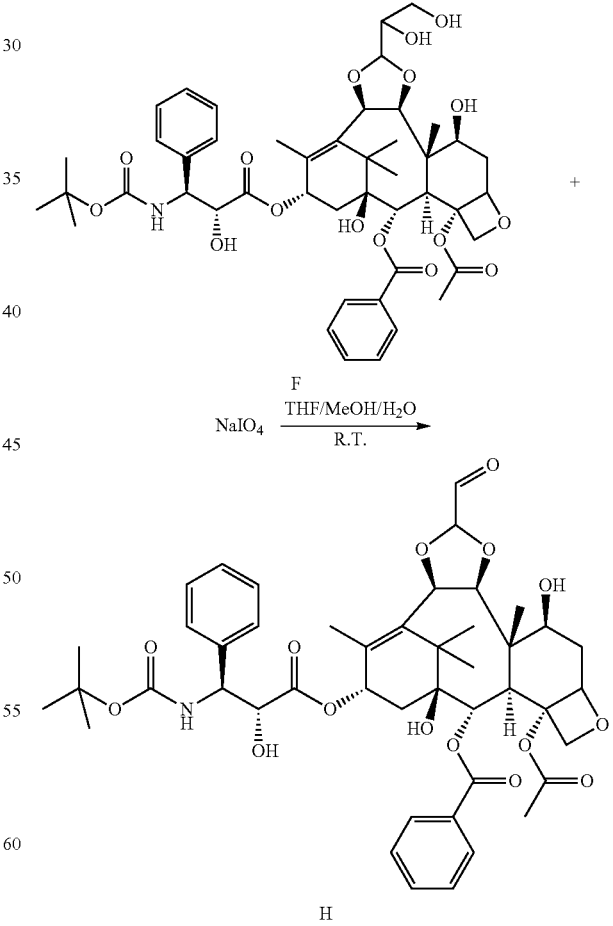

The resulting compound from step 6, 9β-13-O-[(2R,3S)-3-(tert-butyloxycarbonyl amino)-2-hydroxyl-3-phenylpropionyl]-10-deacetyl-9-dihydro-9,10-O-(2,3-dihydroxylpropylidene) baccatinIII G (0.556 g, 0.63 mmol, 1.0 eq) was dissolved into a mixed solution of 7 ml tetrahydrofuran, 7 ml methanol and 7 ml water to form a solution at room temperature. And then, under stirring, sodium periodate (0.887 g, 4.16 mmol, 6.6 eq) was added into the solution to form a mixture. Upon completion of the addition, the mixture was stirred for 2 hours at room temperature. It is shown that the starting materials are completely reacted during the reaction according to the Point-plate tracking (dichloromethane:methanol=20:1). The resulting mixture was added with 50 ml water and 50 ml brine, extracted with ethyl acetate (80 ml×3). The combined organic extracts were washed with 25 ml water and 25 ml brine, dried with anhydrous sodium sulfate, filtered and concentrated under reduced pressure to provide 9β-13-O-[(2R,3S)-3-(tertbutyloxycarbonylamino)-2-hydroxyl-3-phenylpropionyl]-10-deacetyl-9-dihydro-9,10 acetaldehydebaccatinIII Et (0.582 g, white-like solid) which was used as following.

Example 1

9β-13-O-[(2R,3S)-3-(tert-butyloxycarbonylamino)-2-hydroxyl-3-phenyl propionyl]-10-deacetyl-9-dihydro-9,10-O-[2-N-(2S,4S)-2-oxa-5-aza-bicyclo[2.2.1]hept-5-ylmethyl]baccatinIII

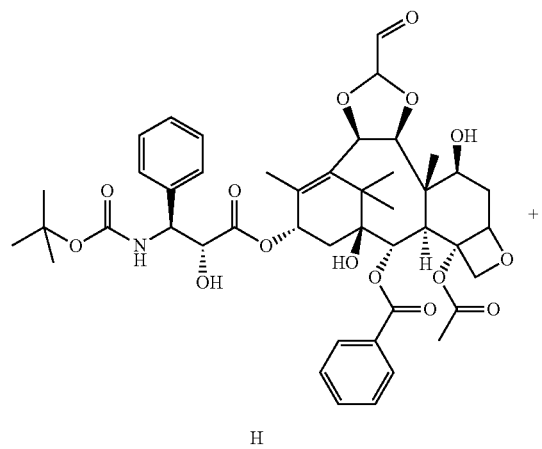

H

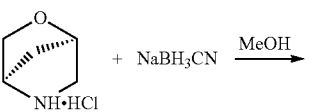 + NaBH₃CN →(MeOH)

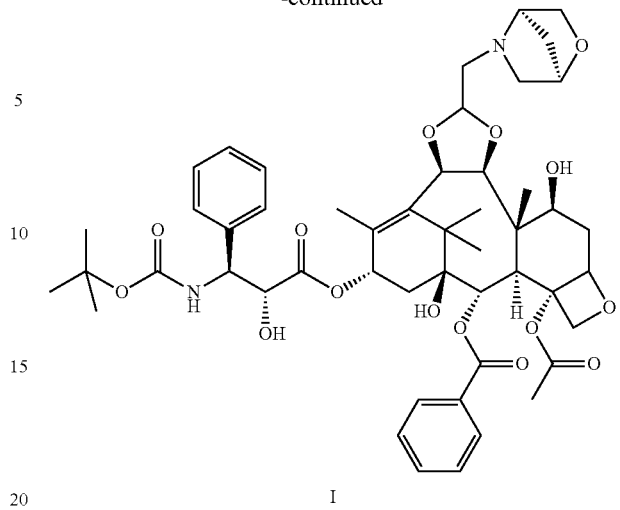

I

The resulting compound from step 7, 9β-13-O-[(2R,3S)-3-(tert-butyloxycarbonyl amino)-2-hydroxyl-3-phenylpropionyl]-10-deacetyl-9-dihydro-9,10-O-acetaldehydebaccatinIII H (0.545 g, 0.63 mmol, 1.0 eq) was dissolved in 30 ml anhydrous methanol in a 100 ml three-neck flask to form a solution under an argon atmosphere. A minor amount of drying molecular sieve (4 Å) and (S,S)-2-oxa-5-aza-bicyclo[2.2.1]heptane hydrochloride (0.568 g, 4.16 mmol, 6.6 eq) were then added into the solution during stirring at room temperature to form a mixture. Upon completion of the addition, the mixture was stirred for 30 minutes at room temperature. Sodium cyanoborohydride (0.261 g, 4.16 mmol, 6.6 eq) was added into the mixture. Upon completion of the addition, the mixture was stirred for 1.5 hours at room temperature. It is shown that the starting materials are completely reacted during the reaction according to the Point-plate tracking (dichloromethane:ethyl acetate:methanol=10:10:1). The resulting mixture was quenched with 70 ml saturated sodium bicarbonate solution, extracted with ethyl acetate (100 ml×4) to form the organic extracts. The combined organic extracts were washed with 25 ml water and 25 ml saturated brine, dried over anhydrous sodium sulfate, filtered and concentrated under reduced pressure to form a residue. The residue was purified by silica gel column chromatography with hexane:dichloromethane:ethyl acetate:methanol=20:10:10:2 as eluents firstly, then with dichloromethane:ethyl acetate:methanol=30:10:2 to provide 9β-13-O-[(2R,3S)-3-(tert-butyloxycarbonylamino)-2-hydroxyl-3-phenylpropionyl]-10-deacetyl-9-dihydro-9,10-O-[2-N-(2S,4S)-2-Oxa-5-aza-bicyclo[2.2.1]hept-5-ylmethyl]baccatinIII (0.412 g, white-like solid) with a yield of 70%.

Rf=0.29 (dichloromethane:ethyl acetate:methanol=10:10:1(V/V))

MW-933, ESI-MS: [M+H]⁺=933.9.

¹H-NMR (CD₃Cl₃, 400 MHz): δ8.1 (d, J=7.5 Hz, 2H, Ar—H), 7.7-7.5 (t, J=7.0 Hz, 1H, Ar—H), 7.5-7.2 (m, 7H), 6.1-6.0 (m, 2H), 5.7-5.6 (d, J=9.4 Hz, 1H), 5.3 (d, J=9.4 Hz, 1H), 5.2 (d, J=7.0 Hz, 1H), 5.1 (s, 1H), 5.0-4.9 (b, 1H), 4.7-4.6 (d, J=8.2 Hz, 1H), 4.6 (b, 1H), 4.4 (b, 1H), 4.4-4.2 (dd, AB-type, J=8.4 Hz, 2H), 4.2-4.0 (m, 2H), 4.0 (d, J=7.9 Hz, 1H), 3.8 (d, J=7.1 Hz, 1H), 3.7-3.6 (d, J=7.8 Hz, 1H), 3.6 (b, 1H), 3.1-3.0 (m, 2H), 3.0-2.9 (m, 1H), 2.9 (d, J=4.7 Hz, 1H), 2.7 (m, J=10.2 Hz, 1H), 2.4 (dd, J=9.7 Hz, J'=14.6 Hz, 1H), 2.3 (s, 3H, CH₃), 2.3-2.2 (m, 1H), 2.2-2.0 (m, 2H), 1.9 (b, 1H), 1.9-1.8 (m, 1H), 1.8-1.7 (m, 1H), 1.65 (s, 3H, CH$_3$), 1.60 (s, 3H, CH$_3$), 1.55 (s, 3H, CH$_3$), 1.4 (s, 9H, t-Bu), 1.3 (s, 3H, CH$_3$).

Example 2

9β-13-O-[(2R,3S)-3-(tert-butyloxycarbonylamino)-2-hydroxyl-3-phenyl propionyl]-10-deacetyl-9-dihydro-9,10-O-[2-N-(2R,4R)-2-oxa-5-aza-bicyclo[2.2.1]hept-5-ylmethyl]baccatinIII The title compound was prepared under the same processes as described in Example 1 by reacting the resulting compound H from step 7, 9β-13-O-[(2R,3S)-3-(tert-butyloxycarbonylamino)-2-hydroxyl-3-phenylpropionyl]-10-deacetyl-9-dihydro-9,10-O-acetaldehydebaccatinIII H with (R,R)-2-oxa-5-aza-bicyclo[2.2.1]heptane hydrochloride as the starting materials to provide 9β-13-O-[(2R,3S)-3-(tert-butyloxycarbonylamino)-2-hydroxyl-3-phenylpropionyl]-10-deacetyl-9-dihydro-9,10-O-[2-N-(2R,4R)-2-oxa-5-aza-bicyclo[2.2.1]hept-5-ylmethyl]baccatinIII J (0.4 g, white-like solid) with a yield of 68%.

Rf=0.32 (dichloromethane:ethyl acetate:methanol=10:10:1(V/V)).

MW=933, ESI-MS: [M+H]$^+$=933.9.

$^1$H-NMR (CD$_3$Cl$_3$, 400 MHz): δ8.11 (d, J=7.3 Hz, 2H, Ar—H), 7.59 (t, J=7.3 Hz, 1H, Ar—H), 7.19-7.53 (m, 7H), 6.1-6.0 (m, 2H), 5.6 (d, J=9.0 Hz, 1H), 5.3 (d, J=7.1 Hz, 1H), 5.2 (d, J=7.0 Hz, 1H), 5.1 (s, 1H), 5.0 (b, 1H), 4.7-4.6 (d, J=7.8 Hz, 1H), 4.6 (s, 1H), 4.5-4.4 (s, 1H), 4.4-4.3 (dd, AB-type, J=8.2 Hz, 2H), 4.2-4.0 (m, 3H), 3.8 (d, J=7.0 Hz, 1H), 3.7 (d, J=8.5 Hz, 1H), 3.6 (b, 1H), 3.1 (m, 1H), 3.1-2.9 (m, 2H), 2.9 (d, J=4.7 Hz, 1H), 2.7 (m, 1H), 2.4 (dd, J=9.8 Hz, J'=14.9 Hz, 1H), 2.3 (s, 3H, CH$_3$), 2.3-2.2 (m, 1H), 2.2-2.0 (m, 2H), 1.9 (b, 1H), 1.8 (m, 1H), 1.7-1.6 (m, 1H), 1.7 (s, 3H, CH$_3$), 1.65 (s, 3H, CH$_3$), 1.6 (s, 3H, CH$_3$), 1.4 (s, 9H, t-Bu), 1.3 (s, 3H, CH$_3$).

Example 3

9β-13-O-[2R,3S)-3-(tert-butyloxycarbonylamino)-2-hydroxyl-3-phenyl propionyl]-10-deacetyl-9-dihydro-9,10-O-(2-methoxylmethylaminoethylidene)baccatinIII

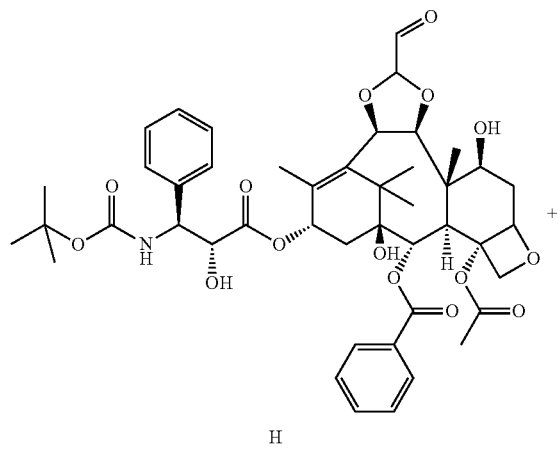

H

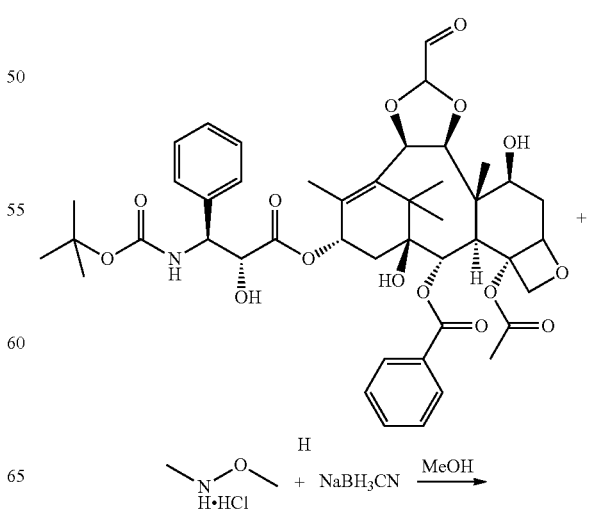

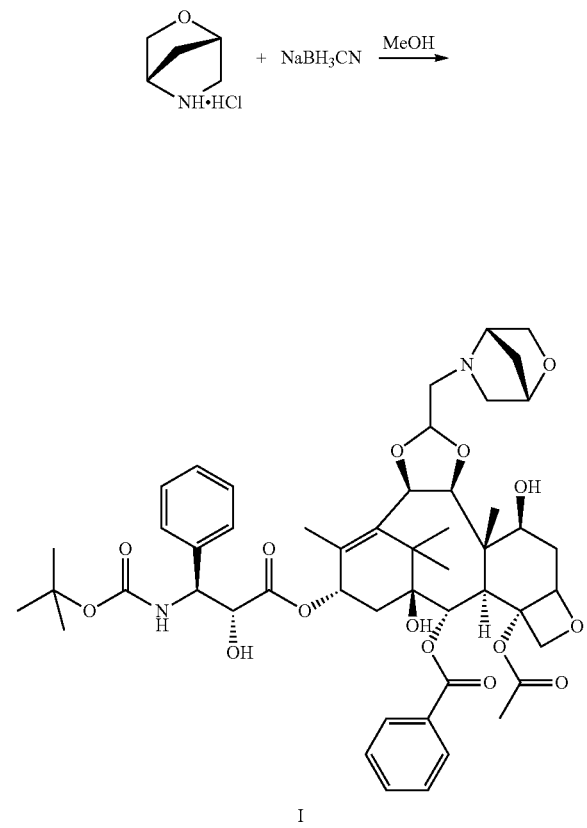

I

-continued

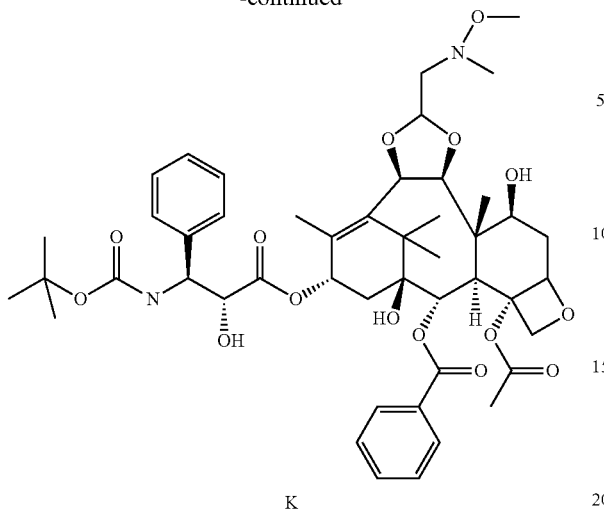

K

The title compound was prepared under the same processes as described in Example 1 by reacting the resulting compound H from step 7, 9β-13-O-[(2R,3S)-3-(tert-butyloxycarbonylamino)-2-hydroxyl-3-phenylpropionyl]-10-deacetyl-9-dihydro-9,10-O-acetaldehydebaccatinIII H with O,N-Dimethyl-hydroxylamine hydrochloride as the starting materials to provide 9β-13-O-[(2R,3S)-3-(tert-butyloxycarbonyl amino)-2-hydroxyl-3-phenylpropionyl]-10-deacetyl-9-dihydro-9,10-O-(2-methoxylmethylaminoethylidene) baccatinIII K (0.48 g, white-like solid) with a yield of 85%.

Rf=0.39 (hexane:ethyl acetate:methanol=20:20:1(V/V)).

MW=895, ESI-MS: [M+H]⁺=895.7, [M+Na]⁺=917.6.

¹H-NMR (CD₃Cl₃, 400 MHz): δ8.1 (d, J=7.4 Hz, 2H, Ar—H), 7.6 (t, J=7.1 Hz, 1H, Ar—H), 7.5-7.2 (m, 7H), 6.2-6.0 (m, 2H), 5.7-5.6 (m, 1H), 5.3 (d, J=6.6 Hz, 1H), 5.2 (d, J=6.3 Hz, 1H), 5.1 (b, 1H), 5.1-5.0 (b, 1H), 4.7-4.4 (m, 1H), 4.6 (b, 1H), 4.4-4.2 (dd, AB-type, J=8.6 Hz, 2H), 4.2 (m, 1H), 4.1 (m, 1H), 3.8 (d, J=6.6 Hz, 1H), 3.6-3.5 (s, 3H, OCH₃), 3.1-3.0 (m, 2H), 2.95 (b, 1H), 2.9 (m, 1H), 2.85 (b, 1H), 2.7-2.6 (s, 3H, NCH₃), 2.4-2.3 (dd, J=10.8 Hz, J'=14.1 Hz, 1H), 2.3 (s, 3H, CH₃), 2.3-2.0 (m, 1H), 1.9 (b, 1H), 1.7 (s, 3H, CH₃), 1.60 (s, 3H, CH₃), 1.55 (s, 3H, CH₃), 1.4 (s, 9H, t-Bu), 1.3 (s, 3H, CH₃).

Example 4

9β-13-O-[(2R,3S)-3-(tert-butyloxycarbonylamino)-2-hydroxyl-3-phenyl propionyl]-10-deacetyl-9-dihydro-9,10-[2-N-(4-pyrrolidin)-piperidine ethylidene]baccatinIII

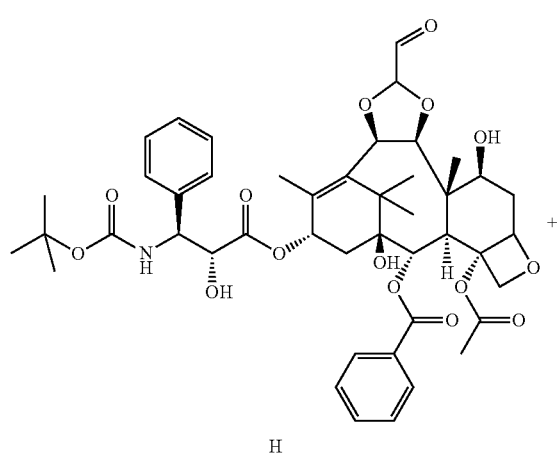

H

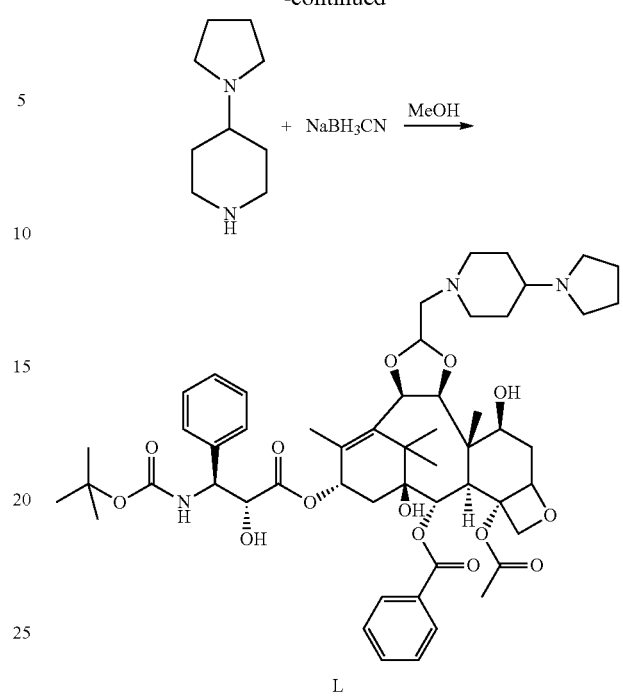

L

The title compound was prepared under the same processes as described in Example 1 by reacting the resulting compound H from step 7, 9β-13-O-[(2R,3S)-3-(tert-butyloxycarbonylamino)-2-hydroxyl-3-phenylpropionyl]-10-deacetyl-9-dihydro-9,10-O-acetaldehydebaccatinIII H with 4-pyrrolidin-1-yl-piperidine as starting materials to provide 9β-13-O-[(2R,3S)-3-(tert-butyloxycarbonylamino)-2-hydroxyl-3-phenylpropionyl]-10-deacetyl-9-dihydro-9,10-[2-N-(4-pyrrolidin)-piperidine-ethylidene]baccatinIII L (0.402 g, white-like solid) with a yield of 64.5%.

Rf=0.29 (dichloromethane:methanol: triethylamine-40:4: 0.25(V/V)).

MW=988, ESI-MS: [M+H]⁺=988.9

¹H-NMR (CD₃Cl₃, 400 MHz): δ8.1 (d, J=7.6 Hz, 2H, Ar—H), 7.6 (t, J=7.4 Hz, 1H, Ar—H), 7.5-7.2 (m, 7H), 6.1 (b, 2H), 6.0 (d, J=4.7 Hz, 1H), 5.7 (d, J=9.8 Hz, 1H), 5.2 (d, J=7.4 Hz, 1H), 5.1 (b, 1H), 5.0 (t, J=4.4 Hz, 1H), 4.7 (d, J=8.2 Hz, 1H), 4.6 (b, 1H), 4.4-4.2 (dd, AB-type, J=8.6 Hz, 2H), 4.1-4.0 (m, 1H), 3.8 (d, J=7.4 Hz, 1H), 3.2-3.0 (m, 6H), 2.9 (b, 1H), 2.8-2.7 (m, 2H), 2.3 (s, 3H, CH₃), 2.3-1.9 (m, 12H), 1.9 (s, 1H), 1.9-1.8 (m, 1H), 1.65 (s, 3H), 1.55 (s, 3H), 1.5 (s, 3H), 1.4 (s, 9H, t-Bu), 1.3 (s, 3H), 1.4-1.3 (m, 2H), 1.3-1.2 (m, 2H).

Example 5

9β-13-O-[(2R,3S)-3-(tert-butyloxycarbonylamino)-2-hydroxyl-3-phenyl propionyl]-10-deacetyl-9-dihydro-9,10-[2-N—(S)-(2-pyrrolidin-1-methyl)-piperidine ethylidene]baccatinIII

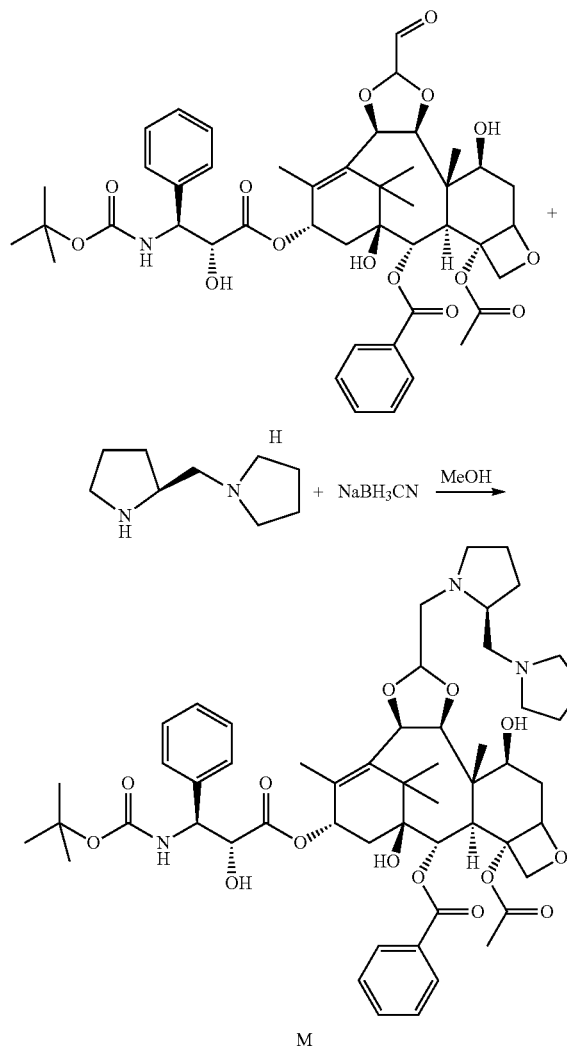

The title compound was prepared under the same processes as described in Example 1 by reacting the resulting compound H from step 7, 9β-13-O-[(2R,3S)-3-(tert-butyloxycarbonylamino)-2-hydroxyl-3-phenylpropionyl]-10-deacetyl-9-dihydro-9,10-O-acetaldehydebaccatinIII H with (S)-(+)-1-(2-pyrrolidin methyl)pyrrolidin as starting materials to provide 9β-13-O-[(2R,3S)-3-(tert-butyloxycarbonylamino)-2-hydroxyl-3-phenylpropionyl]-10-deacetyl-9-dihydro-9,10-O-[2-N—(S)-(2-pyrrolidin-1-methyl)-piperidine ethylidene]baccatinIII M (0.457 g, white-like solid) with a yield of 73.3%.

Rf=0.2 (dichloromethane:methanol: triethylamine-40:2: 0.25(V/V)).

MW=988, ESI-MS: [M+H]$^+$=988.8

$^1$H-NMR (CD$_3$Cl$_3$, 400 MHz): δ8.1 (d, J=7.6 Hz, 2H), 7.6 (t, J=7.4 Hz, 1H), 7.5-7.2 (m, 7H), 6.1 (b, 1H), 6.0 (d, J=5.1 Hz, 1H), 5.7-5.6 (d, J=9.8 Hz, 1H), 5.2 (d, J=7.5 Hz, 1H), 5.1 (b, 1H), 5.0 (t, J=4.5 Hz, 1H), 4.6 (b, 1H), 4.4-4.2 (dd, AB-type, J=8.6 Hz, 2H), 4.1-4.0 (b, 1H), 3.8 (d, J=7.0 Hz, 1H), 3.3-3.2 (m, 2H), 3.0-2.8 (m, 6H), 2.8-2.6 (m, 2H), 2.6-2.4 (m, 1H), 2.4-2.3 (dd, J=9.8 Hz, J'=15.3 Hz, 1H), 2.3 (s, 3H, CH$_3$), 2.3-2.0 (m, 4H), 1.9 (b, 5H), 1.9-1.7 (m, 4H), 1.7 (s, 3H, CH$_3$), 1.6 (m, 5H), 1.4 (s, 9H, t-Bu), 1.4-1.3 (t, 2H), 1.3 (s, 3H, CH$_3$).

Example 6

9β-13-O-[(2R,3S)-3-(tert-butyloxycarbonylamino)-2-hydroxyl-3-phenyl propionyl]-10-deacetyl-9-dihydro-9,10-O-[2-(2-fluoro-ethyl)-methylamino ethylidene]baccatinIII

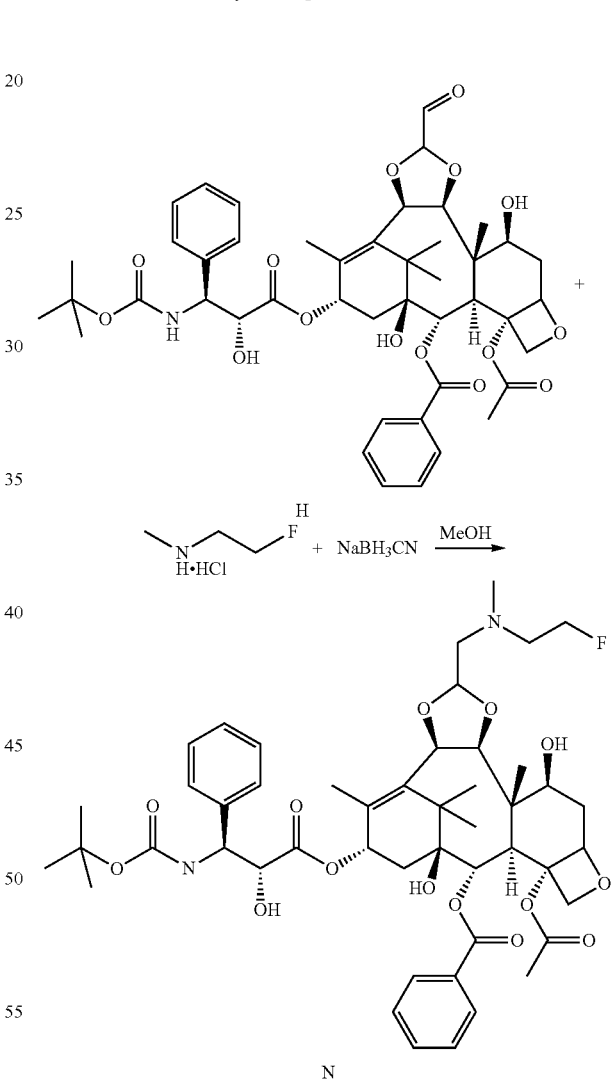

The title compound was prepared under the same processes as described in Example 1 by reacting the resulting compound H from step 7, 9β-13-O-[(2R,3S)-3-(tert-butyloxycarbonylamino)-2-hydroxyl-3-phenylpropionyl]-10-deacetyl-9-dihydro-9,10-O-acetaldehyde baccatinIII H with (2-fluoro-ethyl)-methyl-amine acetate as starting materials to provide 9β-13-O-[(2R,3S)-3-(tert-butyloxycarbonylamino)-2-hydroxyl-3-phenylpropionyl]-10-deacetyl-9-dihydro-9,10-O-

[2-(2-fluoro-ethyl)-methylamino ethylidene]baccatinIII N (0.322 g, white-like solid) with a yield of 56%.

Rf=0.17 (dichloromethane:methanol: triethylamine=10:10:1(V/V)).

MW=911, ESI-MS: [M+H]$^+$=911.8

$^1$H-NMR (CD$_3$Cl$_3$, 400 MHz): δ8.1 (d, J=7.0 Hz, 2H), 7.6 (t, J=7.0 Hz, 1H), 7.5-7.2 (m, 7H), 6.1-6.0 (m, 2H), 5.7 (d, J=9 Hz, 1H), 5.3 (d, J=8 Hz, 1H), 5.1 (b, 1H), 5.0 (b, 1H), 4.6 (b, 2H), 4.5 (t, J=5 Hz, 1H), 4.4-4.2 (dd, AB-type, J=8 Hz, 1H), 4.1 (b, 1H), 3.8 (d, J=7 Hz, 1H), 3.0-2.8 (m, 6H), 2.5 (s, 31-1, CH$_3$), 2.4 (dd, J=9 Hz, J'=15 Hz, 1H), 2.3 (s, 3H, CH$_3$), 2.3-2.0 (m, 4H), 1.9 (b, 1H), 1.7 (s, 3H, CH$_3$), 1.6 (s, 3H, CH$_3$), 1.55 (s, 3H, CH$_3$), 1.4 (s, 9H, t-Bu), 1.3 (s, 3H, CH$_3$).

Example 7

9β-13-O-[2R,3S)-3-(tert-butyloxycarbonylamino)-2-hydroxyl-3-phenyl propionyl]-10-deacetyl-9-dihydro-9,10-O-[2-N—(R)-(2-pyrrolidin-1-methyl)-piperidine ethylidene]baccatinIII

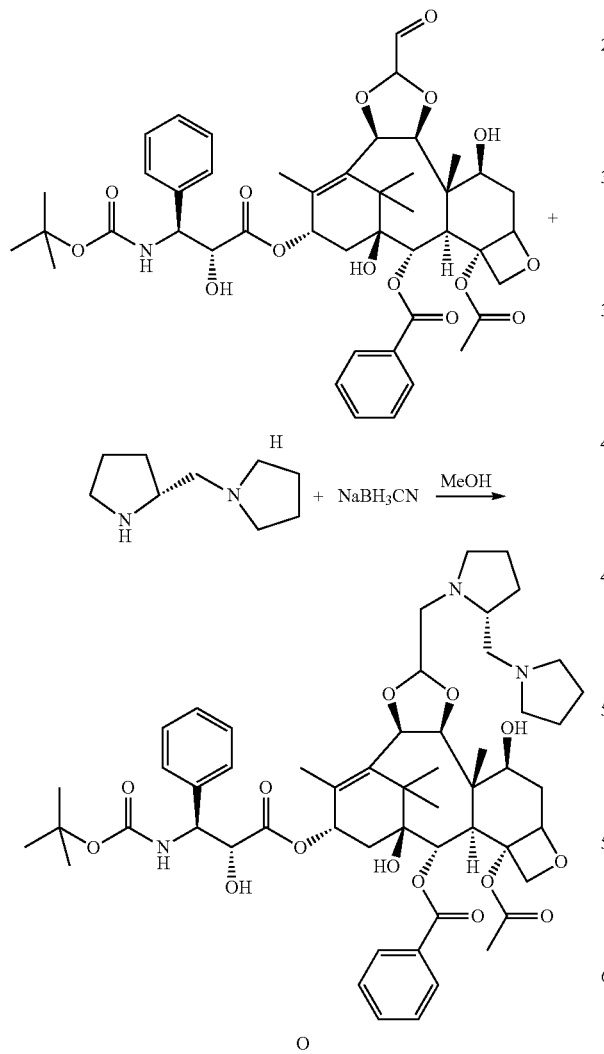

The title compound was prepared under the same processes as described in Example 1 by reacting the resulting compound II from step 7, 9β-13-O-[(2R,3S)-3-(tert-butyloxycarbonylamino)-2-hydroxyl-3-phenylpropionyl]-10-deacetyl-9-dihydro-9,10-O-acetaldehy baccatinIII H with (R)-(+)-1-(2-pyrrolidin methyl)pyrrolidin as starting materials to provide 9β-13-O-[(2R,3S)-3-(tert-butyloxycarbonylamino)-2-hydroxyl-3-phenylpropionyl]-10-deacetyl-9-dihydro-9,10-[2-N—(R)-(2-pyrrolidin-1-methyl)-piperidine ethylidene]baccatinIII O (0.362 g, white-like solid) with a yield of 58%.

Rf=0.28 (hexane:ethyl acetate:methanol: triethylamine=20:20:1:1(V/V)).

MW=988, ESI-MS: [M+H]$^+$-988.9

$^1$H-NMR (CD$_3$Cl$_3$, 400 MHz): δ8.1 (d, J=7.6 Hz, 2H), 7.6 (t, J=7.4 Hz, 1H), 7.5-7.2 (m, 7H), 6.1-6.0 (m, 2H), 5.7-5.6 (d, J=9.4 Hz, 1H), 5.3 (d, J=10.3 Hz, 1H), 5.2 (d, J=7.3 Hz, 1H), 5.1 (s, 1H), 5.0 (dd, AB-type, J=3.4 Hz, J'=6.4 Hz, 1H), 4.7 (b, 1H), 4.6 (s, 1H), 4.4-4.3 (dd, AB-type, J=8.6 Hz, 1H), 4.2 (b, 1H), 4.1 (m, 1H), 3.8 (d, J=7.3 Hz, 1H), 3.3-3.2 (m, 2H), 2.9 (m, 1H), 2.8-2.4 (m, 1H), 2.4-2.3 (m, 1H), 2.3 (s, 3H, CH$_3$), 2.3-1.9 (m, 4H), 1.9 (s, 1H), 1.9-1.7 (m, 1H), 1.7 (s, 311, CH$_3$), 1.6 (m, 5H), 1.4 (s, 9H, t-Bu), 1.3 (s, 3H, CH$_3$).

Example 8

9β-13-O-[(2R,3S)-3-(tert-butyloxycarbonylamino)-2-hydroxyl-3-phenyl propionyl]-10-deacetyl-9-dihydro-9,10-O-[2-N-(4-morpholine)-piperidine ethylidene]baccatinIII

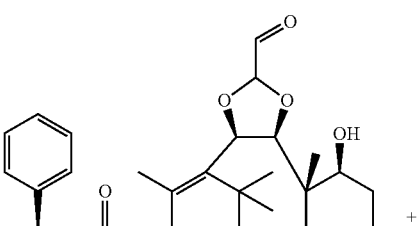

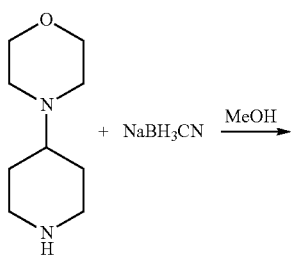

-continued

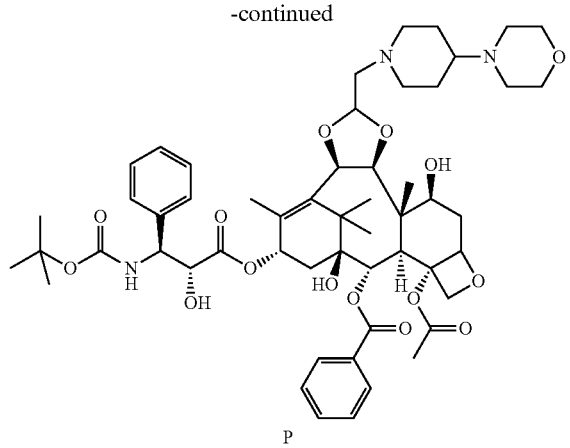

P

The title compound was prepared under the same processes as described in Example 1 by reacting the resulting compound II from step 7, 9β-13-O-[(2R,3S)-3-(tert-butyloxycarbonylamino)-2-hydroxyl-3-phenylpropionyl]-10-deacetyl-9-dihydro-9,10-O-acetaldehy baccatinIII H with 4-piperidin-4-yl-morpholine as starting materials to provide 9β-13-O-[(2R,3S)-3-(tert-butyloxycarbonylamino)-2-hydroxyl-3-phenylpropionyl]-10-deacetyl-9-dihydro-9,10-[2-N-(4-morpholine)-piperidine ethylidene]baccatinIII P (0.47 g, white-like solid) with a yield of 74.4%.

Rf=0.18 (hexane:ethyl acetate:methanol: triethylamine=30:10:3:2(V/V)).

MW=1004, ESI-MS: [M+H]$^+$=1004.9

$^1$H-NMR (CD$_3$Cl$_3$, 400 MHz): δ8.1 (d, J=7.5 Hz, 2H), 7.6 (t, J=7.4 Hz, 1H), 7.5-7.2 (m, 7H), 6.1-6.0 (m, 2H), 5.6 (d, J=9.8 Hz, 1H), 5.3 (d, J=6.6 Hz, 1H), 5.2 (d, J=6.3 Hz, 1H), 5.1 (b, 2H), 5.0 (b, 1H), 4.7 (d, J=8.2 Hz, 1H), 4.6 (b, 1H), 4.4-4.3 (dd, AB-type, J=8.5 Hz, 2H), 4.0 (m, 1H), 3.8 (d, J=7.2 Hz, 1H), 3.8-3.7 (m, 4H), 3.2-3.0 (m, 2H), 2.9-2.8 (m, 1H), 2.8-2.7 (m, 2H), 2.6-2.5 (m, 4H), 2.4-2.3 (dd, J=9.8 Hz, J'=15.3 Hz, 1H), 2.3 (s, 3H, CH$_3$), 2.3-2.0 (m, 6H), 1.9 (b, 1H), 1.9-1.7 (m, 2H), 1.7 (s, 3H, CH$_3$), 1.65 (s, 3H, CH$_3$), 1.55 (s, 3H, CH$_3$), 1.4 (s, 3H), 1.3 (s, 9H-1, t-Bu).

Example 9

9β-13-O-[(2R,3S)-3-(tert-butyloxycarbonylamino)-2-hydroxyl-3-phenyl propionyl]-10-deacetyl-9-dihydro-9,10-[2-N-(cyclopropylamino)-piperidine ethylidene]baccatinIII

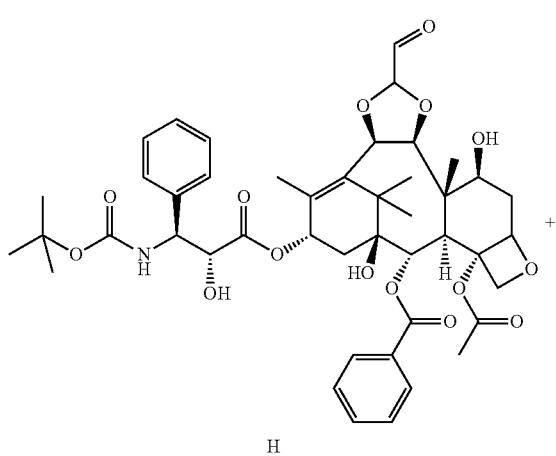

H

-continued

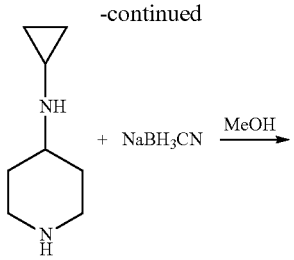

+ NaBH$_3$CN $\xrightarrow{\text{MeOH}}$

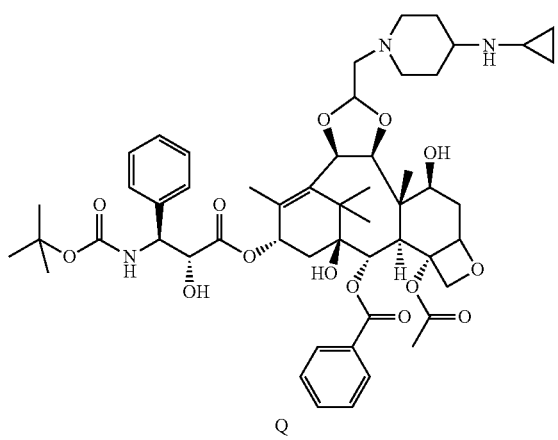

Q

The title compound was prepared under the same processes as described in Example 1 by reacting the resulting compound H from step 7, 9β-13-O-[(2R,3S)-3-(tert-butyloxycarbonylamino)-2-hydroxyl-3-phenylpropionyl]-10-deacetyl-9-dihydro-9,10-O-acetaldehy baccatinIII H with cyclopropyl-piperidin-4-yl-amine as starting materials to provide 9β-13-O-[(2R,3S)-3-(tert-butyloxycarbonylamino)-2-hydroxyl-3-phenylpropionyl]-10-deacetyl-9-dihydro-9,10-O-[2-N-(cyclopropylamino)-piperidine ethylidene]baccatinIII Q (0.29 g, white-like solid) with a yield of 47%.

Rf=0.20 (hexane:dichloromethane:ethyl acetate:methanol=30:10:2:3(V/V)).

MW=974, ESI-MS: [M+H]$^+$=974.9

$^1$H-NMR (CD$_3$Cl$_3$, 400 MHz): δ8.1 (d, J=7.3 Hz, 2H), 7.6 (t, J=7.3 Hz, 1H), 7.5-7.2 (m, 7H), 6.1-6.0 (m, 2H), 5.6 (d, J=9.8 Hz, 1H), 5.3 (d, J=7.5 Hz, 1H), 5.2 (d, J=6.4 Hz, 1H), 5.1 (b, 1H), 5.0 (t, J=3.9 Hz, 1H), 4.7 (d, J=8.3 Hz, 1H), 4.6 (b, 1H), 4.4-4.2 (dd, AB-type, J=18.5 Hz, J'=9.8 Hz, 2H), 4.2-4.1 (m, 1H), 4.1-4.0 (m, 1H), 3.8 (d, J=7.2 Hz, 1H), 3.1-2.7 (m, 5H), 2.6-2.5 (m, 3H), 2.4-2.3 (dd, J=9.8 Hz, J'=15.3 Hz, 1H), 2.3 (s, 3H, CH₃), 2.3-1.9 (m, 9H), 1.9-1.8 (m, 3H), 1.6 (s, 3H, CH₃), 1.55 (s, 3H, CH₃), 1.5 (s, 3H, CH₃), 1.4 (s, 9H, t-Bu), 1.3 (s, 3H, CH₃).

Example 10

9β-13-O-[(2R,3S)-3-(tert-butyloxycarbonylamino)-2-hydroxyl-3-phenyl propionyl]-10-deacetyl-9-dihydro-9,10-O-(2-morpholine ethylidene) baccatinIII

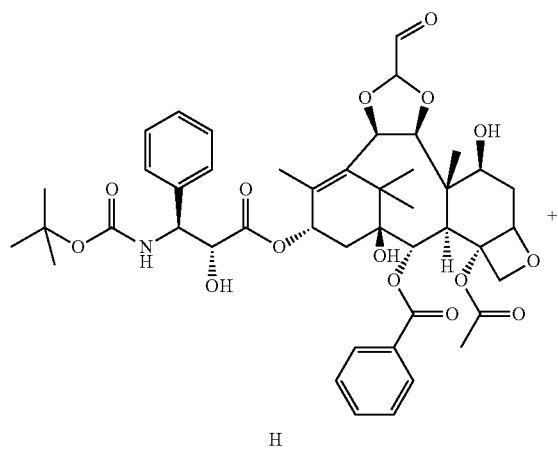

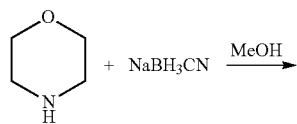

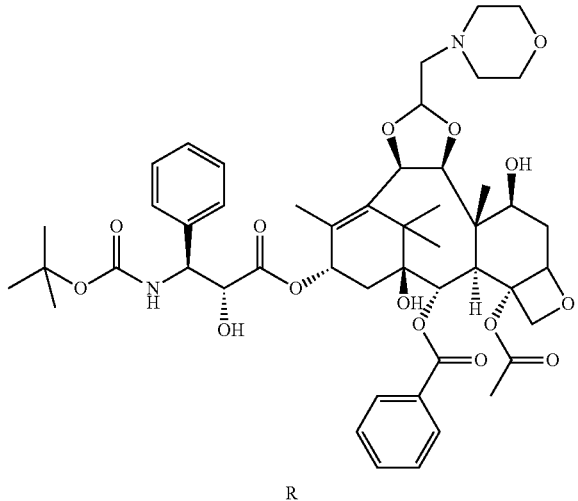

The title compound was prepared under the same processes as described in Example 1 by reacting the resulting compound H from step 7, 9β-13-O-[(2R,3S)-3-(tert-butyloxycarbonylamino)-2-hydroxyl-3-phenylpropionyl]-10-deacetyl-9-dihydro-9,10-O-acetyl baccatinIII H with morpholine as starting materials to provide 9β-13-O-[(2R,3S)-3-(tert-butyloxycarbonylamino)-2-hydroxyl-3-phenylpropionyl]-10-deacetyl-9-dihydro-9,10-O-(2-morpholine ethylidene) baccatin III R (0.517 g, white-like solid with a yield of 89%.

Rf=0.22 (hexane:ethyl acetate:methyl: triethylamine=20:20:1:1(V/V)).

MW=921, ESI-MS: $[M+H]^+$=921.7

$^1$H-NMR (CD₃Cl₃, 400 MHz): δ8.1 (d, J=7.3 Hz, 2H), 7.59 (t, J=7.3 Hz, 1H), 7.5-7.2 (m, 7H), 6.1-6.0 (m, 2H), 5.6 (d, J=10.0 Hz, 1H), 5.3 (d, J=10.0 Hz, 1H), 5.2 (d, J=6.9 Hz, 1H), 5.1 (s, 1H), 5.0 (t, J=3.9 Hz, 1H), 4.7 (d, J=8.3 Hz, 1H), 4.6 (s, 1H), 4.4 (d, J=8.3 Hz, 1H), 4.3 (d, J=8.3 Hz, 1H), 4.2-4.0 (m, 2H), 3.9-3.6 (m, 5H), 2.9 (d, J=4.9, 1H), 2.8-2.7 (dd, AB-type, J=18.4 Hz, J'=4.4 Hz, 2H), 2.7-2.5 (m, 4H), 2.3 (s, 3H), 2.5-1.9 (m, 4H), 1.9 (s, 1H), 1.65 (s, 3H), 1.6 (s, 3H), 1.4 (s, 9H), 1.3 (s, 6H).

TEST EXAMPLE 1

The Therapeutic Effects of SHR-110008 and Taxotere Against Xenografts of Human A549 Non-Small Cell Lung Cancer (NSCLC) Tumors in Nude Mice Test Animals:
 Animal species: BALB/cA-nude mice.
 Numbers of animals: 9 mice in control group, 5 mice in medication administration team.
 Environment: SPF Level.

Test Protocol:
 Animals were adapted in animal house for 1 week and were hypodermic inoculated human A549 NSCLC tumors. After tumors grew to 100-300 mm³, mice were randomly divided into teams of SHR-110008 and Taxotere(d0). The doses of SHR-110008 were 10 and 16 mg/kg, and the doses of Taxotere were 12 and 19 mg/kg, separately. The route of administration is intravenous injection. SHR-110008(10 mg/kg) and Taxotere (12 mg/kg) were administrated on d0, d4, d8, a total of three times. SHR-110008(16 mg/kg) and Taxotere (19 mg/kg) were administrated on d0, d7, a total of two times. The volume of tumors and weights of the mice were measured for 2-3 times per week. The calculation formula of the volume of tumor (V) is: $V=\frac{1}{2}\times a\times b^2$, a: length of tumor, b: width of tumor.

Result:

TABLE 1

Intravenous injection (i.v); the therapeutic effect of SHR110008, Taxotere against xenografts of human A549 NSCLC tumors in nude mice.

| Group | Dose (mg/kg) | Administration | Animal Numbers d0/dn | Body weight (g) d0 | dn | TV (X ± SD, mm³) d0 | dn | RTV X ± SD | T/C (%) |
|---|---|---|---|---|---|---|---|---|---|
| Control | | | 9/9 | 17.5 | 16.2 | 140 ± 15 | 3056 ± 11161 | 22.13 ± 9.5 | |
| SHR-110008 | 10 | d0, 4, 8 | 5/5 | 18.4 | 16.9 | 129 ± 20 | 1383 ± 243 | 10.81 ± 1.79 | 48.8* |

TABLE 1-continued

Intravenous injection (i.v); the therapeutic effect of SHR110008, Taxotere against xenografts of human A549 NSCLC tumors in nude mice.

| Group | Dose (mg/kg) | Administration | Animal Numbers d0/dn | Body weight (g) d0 | Body weight (g) dn | TV (X ± SD, mm³) d0 | TV (X ± SD, mm³) dn | RTV X ± SD | T/C (%) |
|---|---|---|---|---|---|---|---|---|---|
| SHR-110008 | 16 | d0, 7 | 5/5 | 18.0 | 16.6 | 143 ± 38 | 612 ± 340 | 4.41 ± 2.43 | 19.9* |
| Taxotere | 12 | d0, 4, 8 | 5/5 | 17.6 | 14.1 | 140 ± 24 | 1149 ± 627 | 8.65 ± 5.83 | 39.1* |
| Taxotere | 19 | d0, 7 | 5/5 | 17.7 | 13.0 | 134 ± 19 | 902 ± 736 | 7.13 ± 6.00 | 32.2* | d0: the time of the first dosage;
dn: the 14th day after the first dosage;
*P < 0.01 vs control.

TABLE 2

Intravenous injection (i.v); the therapeutic effect of SHR110008, Taxotere against xenografts of human A549 NSCLC tumors in nude mice (weighing method).

| Group | Dose (mg/kg) | Animal Numbers d0/dn | Body weight (g) d0 | Body weight (g) dn | Weight of tumors (g) x ± SD | T/C (%) |
|---|---|---|---|---|---|---|
| Control | | 9  9 | 17.5 | 16.2 | 2.59 ± 1.01 | |
| SHR-110008 | 10 | 5  5 | 18.4 | 16.9 | 1.59 ± 0.57 | 38.6* |
| SHR-110008 | 16 | 5  5 | 18.0 | 16.6 | 0.67 ± 0.23 | 74.1* |
| Taxotere | 12 | 5  5 | 17.6 | 14.1 | 1.25 ± 0.71 | 51.7* |
| Taxotere | 19 | 5  5 | 17.7 | 13.0 | 1.09 ± 0.73 | 57.9* | d0: the time of the first dosage;
dn: the 14th day after the first dosage.
*P < 0.01 vs control.

Conclusion:

Refer to table 1, table 2 and FIG. 1, under the suitable dose schedule, the therapeutic effect and toxicity of SHR110008 were better than that of Taxotere.

TEST EXAMPLE 2

The Therapeutic Effects of SHR1021-47 Against Xenografts of Human A549 Non-Small Cell Lung Cancer (NSCLC) Tumors in Nude Mice Test Animals:
Animal species: BALB/cA-nude mice.
Numbers of animals: 12 mice in control group, 6 mice in medication administration team.

Test Protocol:
Cell culture: Human A549 NSCLC tumor cells were cultured in vitro remaining on logarithmic growth phase.

Transplantation: Take the prepared cells to inoculate subcutaneously to the nude mice.

Inoculation: Take the tumor lump to inoculate in one side of oxter on the condition of asepsis.

Grouping and dose design: Measure the diameter of transplantation tumor by sliding caliper. After tumors grew to 100-250 mm³, mice were randomly divided into groups of Shr1021-47 (8 mg/kg, 12 mg/kg, 16 mg/kg) and Taxotere (12 mg/kg).

Administration route and time: iv administration. Shr1021-47 and Taxotere were administrated on d0, d7, 2 times in all. Measure the volume of tumor and weigh the mice 2-3 times per week.

Evaluation Criterion:
The calculation formula of the volume of tumor(V) is: $V = \frac{1}{2} \times a \times b^2$, a: length of tumor, b: width of tumor. Calculate the relative tumor volume (RTV) according to the measurements. The formula is: $RTV = V_t/V_0$. $V_0$ refers to the volume of tumor on d0; $V_t$ refers to the volume of tumor on every measurement. The index of antitumor activity is T/C(%). The formula is: $T/C(\%) = T_{RTV}/C_{RTV} \times 100$, $T_{RTV}$: RTV of treatment group, $C_{RTV}$: RTV of control group.

Result:

TABLE 3

Intravenous injection (i.v); the therapeutic effect of Shr1021-47 against xenografts of human A549 NSCLC tumors in nude mice.

| Group | Dose (mg/kg) | Animal Numbers d0 | Animal Numbers dn | Body weight(g) d0 | Body weight(g) dn | TV(X ± SD, mm³) d0 | TV(X ± SD, mm³) dn | RTV X ± SD | T/C (%) |
|---|---|---|---|---|---|---|---|---|---|
| Control | | 12 | 12 | 18.7 | 16.9 | 181 ± 29 | 2513 ± 855 | 14.3 ± 5.2 | |
| Shr1021-47 | 8 | 6 | 6 | 18.7 | 16.6 | 168 ± 21 | 2047 ± 279 | 12.3 ± 1.6 | 86.0 |
| Shr1021-47 | 12 | 6 | 6 | 18.5 | 16.3 | 198 ± 47 | 1293 ± 458 | 6.6 ± 2.6 | 46.2* |
| Shr1021-47 | 16 | 6 | 6 | 20.7 | 17.1 | 178 ± 45 | 705 ± 360 | 4.3 ± 2.8 | 30.1* |
| Taxotere | 12 | 6 | 6 | 20.7 | 15.6 | 156 ± 20 | 1679 ± 749 | 11.2 ± 6.0 | 78.3 | d0: the time of the first dosage;
dn: the day which the therapeutic effects were best actually. In this test, dn refers to the 14th day after the first dosage.

Figure 2:
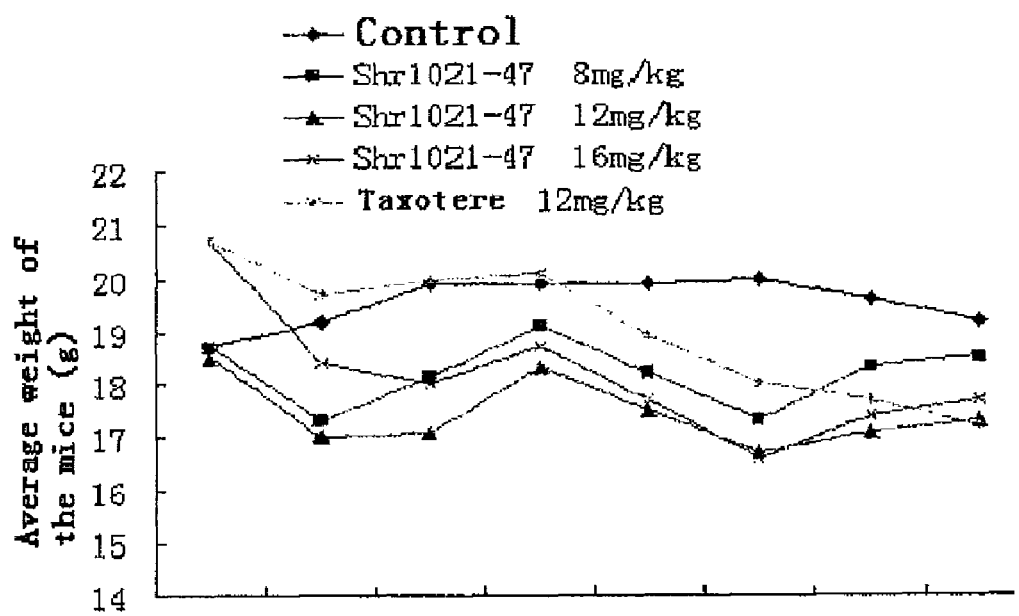
FIG. 2 is the weight effect of compound SHR1021-47 against tumors in nude mice wherein *P<0.01.

Conclusion:

Refer to FIG. 2 and table 3, Shr1021-47 inhibited the growth of human A549 NSCLC tumors in nude mice obviously. Although the toxicity of Shr1021-47 is a little big, but it can be well tolerant to mice. The efficacy of Shr1021-47 is better than Taxotere.

What is claimed is:

1. A compound of the formula (I):

(I)

wherein
R$_1$, R$_2$ and N to which they are attached are composed of the following groups:

$Z_1$ and $Z_2$ are fluorine or $Z_1$ is hydroxyl and $Z_2$ is hydrogen or $Z_1$ is hydroxyl and $Z_2$ is methyl;

$Z_3$ is selected from the group consisting of phenyl, furyl, pyrrolyl, pyridyl and 2-methyl-1-acryl; and $Z_4$ is tert-butoxy.

2. The compound of claim 1, wherein $Z_3$ is phenyl.

3. The compound of claim 1, wherein $Z_3$ is selected from the group consisting of furyl, pyrrolyl, and pyridyl.

4. The compound of claim 1, wherein $Z_3$ is 2-methyl-1-acryl.

5. A salt of the compound of the formula (I):

(I)

wherein
R$_1$, R$_2$ and N to which they are attached are composed of the following groups:

$Z_1$ and $Z_2$ are fluorine or $Z_1$ is hydroxyl and $Z_2$ is hydrogen or $Z_1$ is hydroxyl and $Z_2$ is methyl;

$Z_3$ is selected from the group consisting of phenyl, furyl, pyrrolyl, pyridyl and 2-methyl-1-acryl; and $Z_4$ is tert-butoxy.

6. The salt of the compound of claim 5, wherein $Z_3$ is phenyl.

7. The salt of the compound of claim 5, wherein $Z_3$ is selected from the group consisting of furyl, pyrrolyl, and pyridyl.

8. The salt of the compound of claim 5, wherein $Z_3$ is 2-methyl-1-acryl.

* * * * *